United States Patent
Brugger et al.

(10) Patent No.: US 6,743,193 B2
(45) Date of Patent: Jun. 1, 2004

(54) HERMETIC FLOW SELECTOR VALVE

(75) Inventors: James M. Brugger, Newburyport, MA (US); Jeffrey H. Burbank, Boxford, MA (US)

(73) Assignee: Nx Stage Medical, Inc., Lawrence, MA (US)

(*) Notice: Subject to any disclaimer, the term of this patent is extended or adjusted under 35 U.S.C. 154(b) by 0 days.

(21) Appl. No.: 09/907,872

(22) Filed: Jul. 17, 2001

(65) Prior Publication Data

US 2003/0018290 A1 Jan. 23, 2003

(51) Int. Cl.⁷ .......................... A61M 37/00; A61M 1/00
(52) U.S. Cl. ................. 604/6.1; 604/6.01; 604/4.01; 604/34; 210/424; 137/625.43
(58) Field of Search ................. 604/6.1, 4.01, 604/34, 6.01; 210/93, 118, 137, 141, 144, 117, 124, 129, 133, 424; 137/625.14, 625.11, 625.42, 625.43, 597

(56) References Cited

U.S. PATENT DOCUMENTS

| | | |
|---|---|---|
| 343,251 A | 6/1886 | Neracher |
| 3,744,524 A * | 7/1973 | Blau ................. 137/636 |
| 4,181,610 A | 1/1980 | Shintani et al. ........... 210/85 |
| 4,324,662 A | 4/1982 | Schnell ................. 210/646 |
| 4,614,590 A | 9/1986 | Rath et al. ............... 210/637 |
| 4,636,473 A | 1/1987 | Kleinstreuer ............ 435/289 |
| 4,648,866 A | 3/1987 | Malbrancq et al. ........... 604/5 |
| 4,885,087 A | 12/1989 | Kopf ................. 210/321.72 |
| 5,605,630 A | 2/1997 | Shibata ................. 210/646 |
| 5,687,764 A * | 11/1997 | Tanaka et al. ......... 137/625.43 |
| 5,690,829 A | 11/1997 | Lauer ................. 210/636 |
| 5,830,365 A | 11/1998 | Schneditz ............ 210/739 |
| 5,894,011 A | 4/1999 | Prosl et al. .............. 422/44 |
| 6,177,049 B1 | 1/2001 | Schnell et al. ............ 422/44 |
| 6,189,388 B1 | 2/2001 | Cole et al. ............. 73/861.07 |
| 6,221,040 B1 | 4/2001 | Kleinekofort ............ 604/65 |
| 6,308,737 B1 | 10/2001 | Krivitski |
| 6,572,576 B2 * | 6/2003 | Brugger et al. ........... 604/4.01 |

* cited by examiner

Primary Examiner—Angela D. Sykes
Assistant Examiner—Leslie R. Deak
(74) Attorney, Agent, or Firm—Proskauer Rose LLP

(57) ABSTRACT

A flow diverting appliance has a flexible valve body to which a number of flow lines are connected. The valve body is deformed to create different flow paths within it. The valve body may be deformed, for example, by pinching it to define press-seals in an enclosed volume inside the valve body. The press seals divide the enclosed volume to form exclusive flow channels which allow communication between some flow lines and permit flow communication between other lines. The invention provides a way of making flow diverters part of a replaceable blood circuit which is fully hermetic and with no dead-end spaces which would allow blood to cagulate.

48 Claims, 22 Drawing Sheets

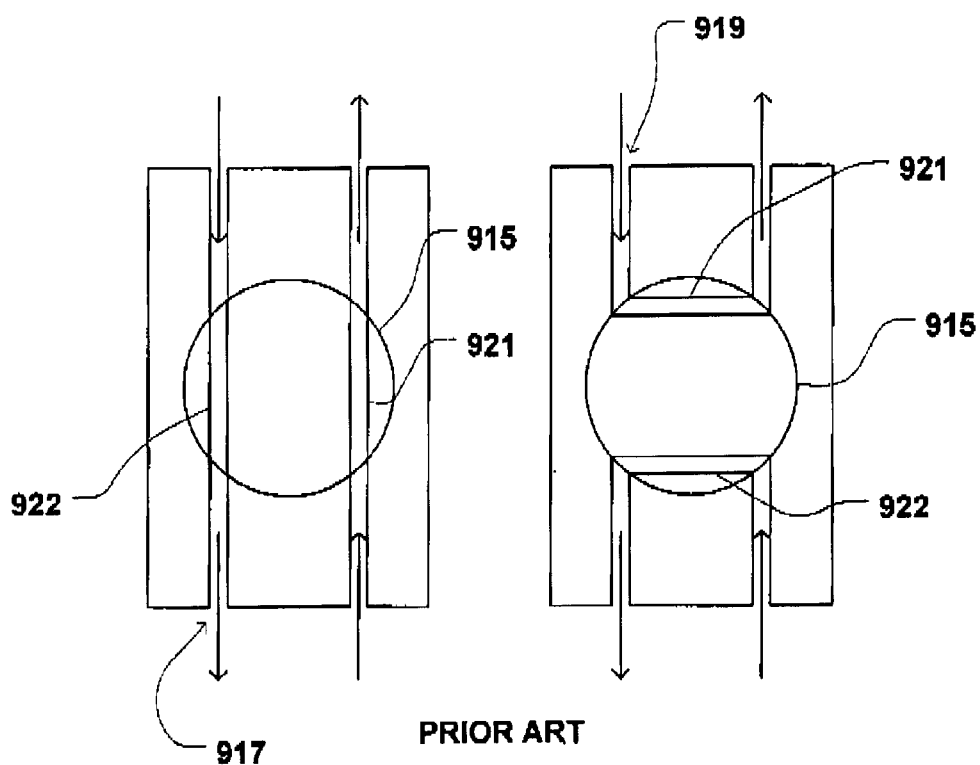
Fig. 1C
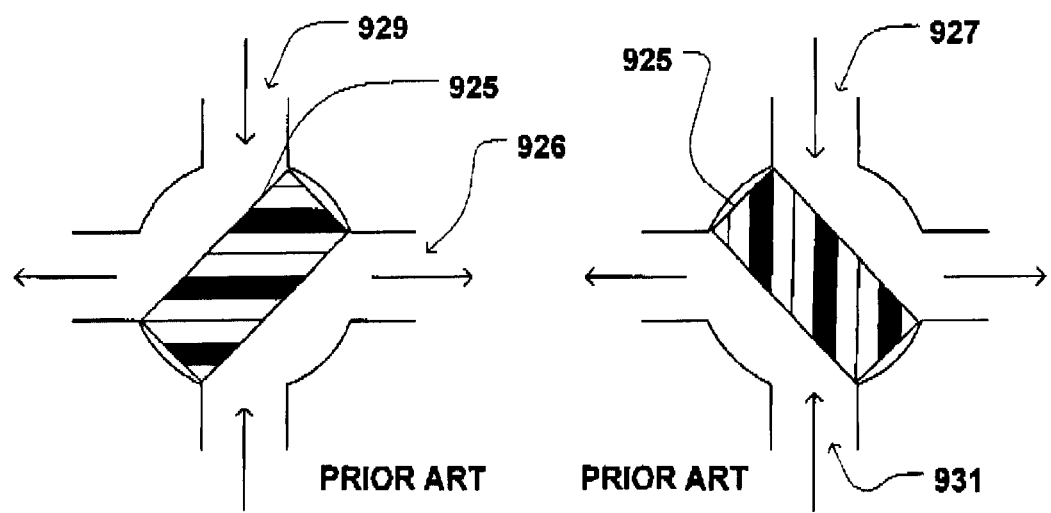
Fig. 1D1   Fig. 1D2

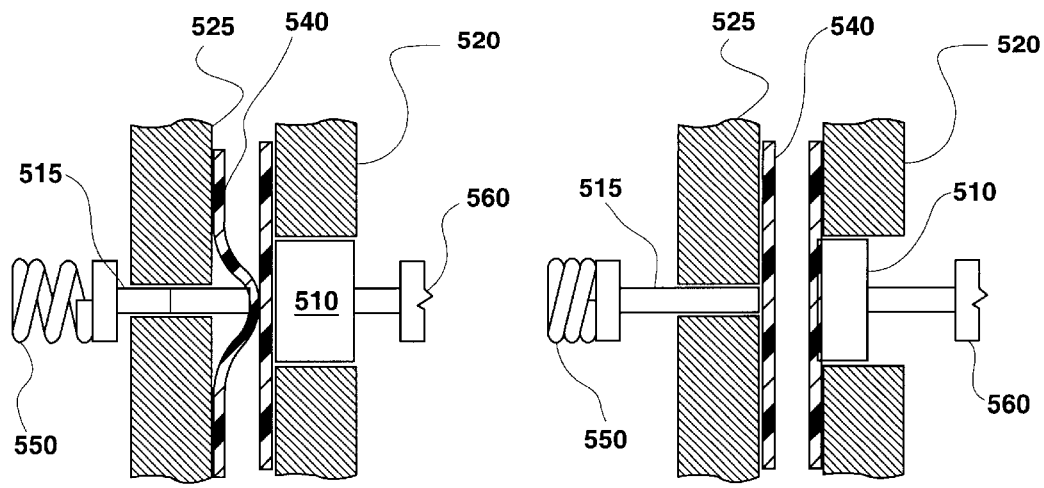
Fig. 13 A
Fig. 13C
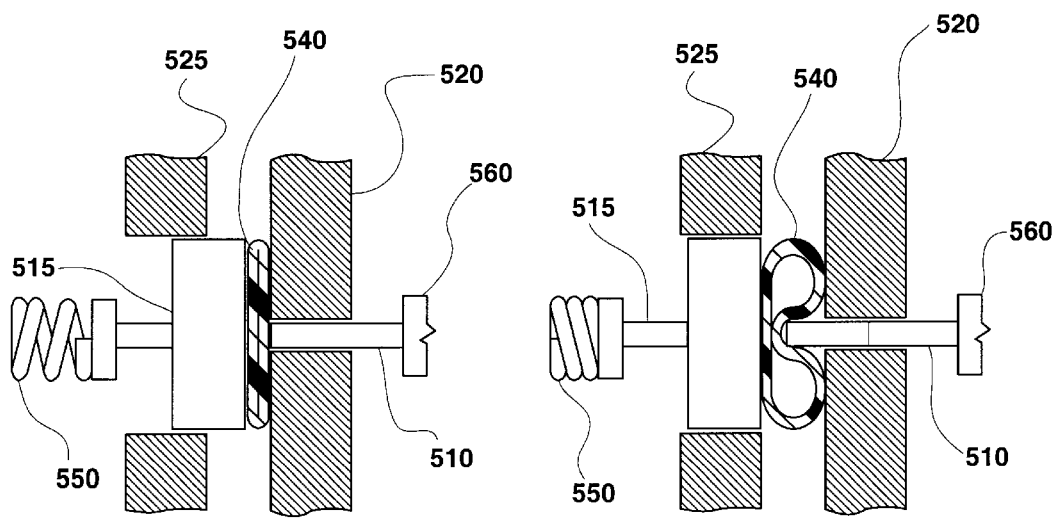
Fig. 13B
Fig. 13 D

Fig. 18G        Fig. 18H

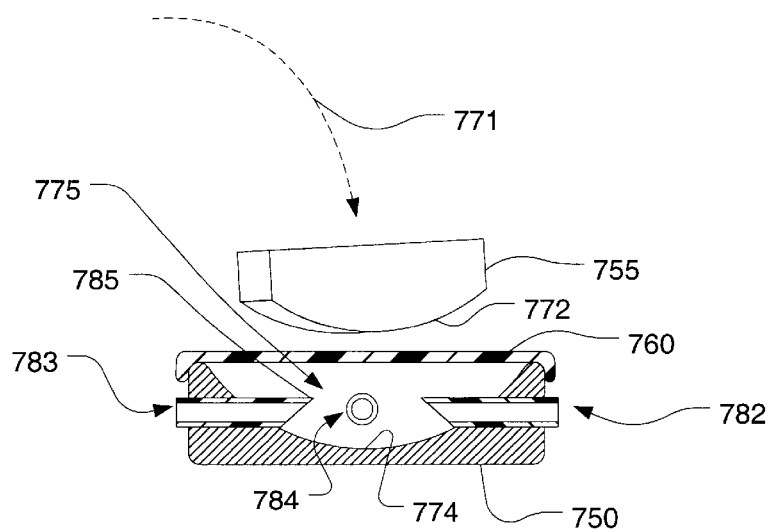
Fig. 19C
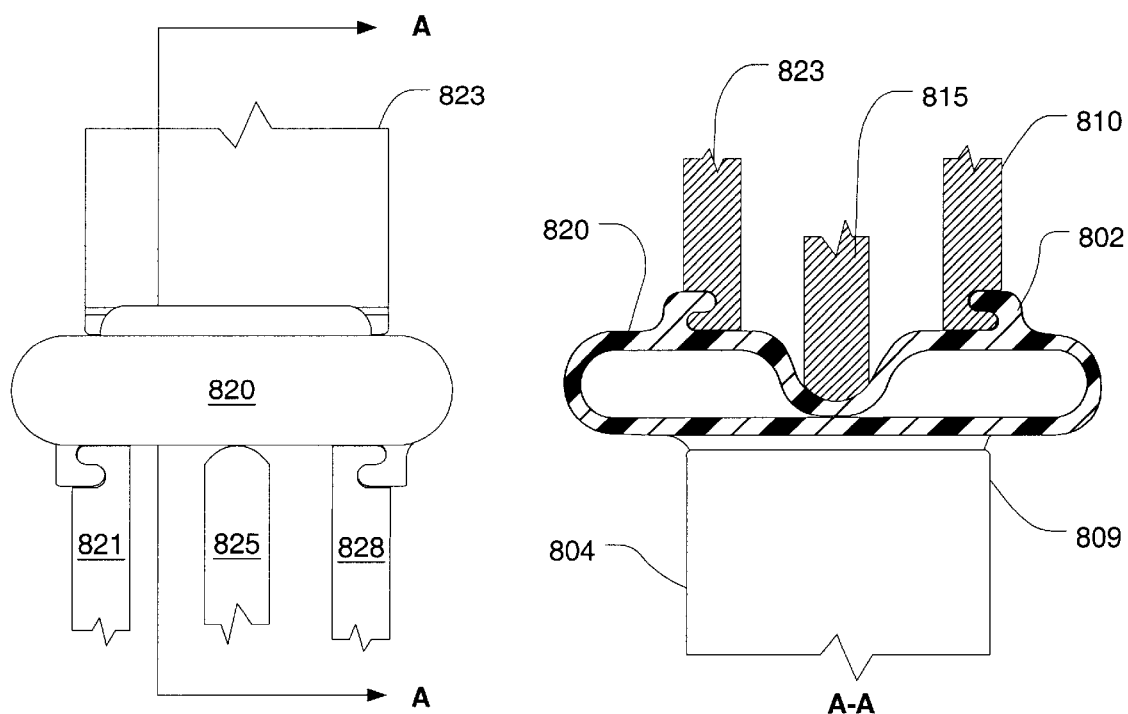
Fig. 20A  Fig. 20B

HERMETIC FLOW SELECTOR VALVE

BACKGROUND OF THE INVENTION

1. Field of the Invention

The invention relates to flow-selector valves and particularly such valves that may be used in disposable sterile fluid lines, for example, lines used for extracorporeal blood processes.

2. Background

Hemofiltration, dialysis, hemodiafiltration, and other extracorporeal blood treatments may employ flow selector valves such as Y-valves, four-way valves, and other such devices for redirecting the flow of blood and other fluids such as replacement fluids. For example, the direction of the flow of blood through certain types of filters may be reversed repeatedly to prevent coagulation of blood in regions where the mean flow slows to very low rates. For example, where blood is circulated through tubular media in the context of a dialysis filter, it has been proposed that blood may coagulate on the surface of the inlet header leading to the progressive coagulation of blood. U.S. Pat. No. 5,605,630, proposes occasionally reversing the flow of blood through the filter. A four-way valve is proposed for changing over the flow direction.

In other references, the idea of reversing the flow of blood through a tubular media filter is discussed in connection with other issues. For example, in U.S. Pat. No. 5,894,011, the known technique of switching access lines in the patient to improve the flow through an occluded fistula is automated by the addition of a four-way valve on the patient-side blood circuit. In single-access systems in general, for example as described in U.S. Pat. No. 5,120,303, flow is conventionally reversed through the filter during each draw/return cycle. In the '303 reference, the specification observes that the efficiency of filtration is increased due to the double-passing of the same blood through the filter; that is, each volume of drawn blood is filtered twice. Yet another reference, U.S. Pat. No. 6,189,388 B1, discusses reversing the flow direction of blood through the patient access occasionally in order to quantify an undesirable short-circuit effect that attends their long term use. Still another U.S. Pat. No. 6,177,049 B1 suggests reversing flow through the draw access before treatment while an observer is present to test the accesses for patency or to clear blockage in the accesses.

In copending commonly assigned application titled "Device And Method For Enhancing Performance Of Membranes And Filters," which is hereby incorporated by reference as if set forth in its entirety herein, a Y-shaped flow selector switch is described in connection with the selective direction of replacement fluid into the blood circuit of a hemofiltration system.

Referring to FIGS. 1A through 1E, a number of alternative designs for four-way valves have been developed for blood circuits. Referring to FIG. 1A, U.S. Pat. No. 5,894,011, discloses a valve that swaps the connections between pairs of lines 905 and 906 via a pair of rotatably connected disks 901 and 902, each of which supports one of the pairs of lines 905 and 906. A seal must be maintained between the disks 901 and 902 and between the respective lines. The device is intended to be operated manually.

Referring to FIG. 1B, another four-way valve, disclosed in U.S. Pat. No. 5,605,630, which has been proposed for use in blood lines, has a rotating wheel 910 with channels 911 and 912 defined between the wheel 910 and the inside of a housing 913. When the wheel is rotated, the channels 911 and 912 shift to join a different pair of lines. This device also has seals.

Referring to FIG. 1C, another arrangement is proposed in U.S. Pat. No. 6,177,049. This device has a rotating component 915 with channels 921 and 922 defined within it. As the rotating component 915 is rotated, the channels defined between pairs of lines 917 and 919 change from parallel lines joining one set of corresponding lines to U-shaped channels joining a different set.

Referring to FIGS. 1D1 and 1D2, a design, disclosed in U.S. Pat. No. 4,885,087, is very similar to that of FIG. 1B. This design has a rotator 925 that connects different pairs of lines depending on the position thereby defining two different sets of possible flow channels 926 and 929 or 927 and 931.

In all of the above designs, the valves are not hermetically sealed. Any seal can be compromised, particularly by microorganisms. Thus, each of the foregoing designs suffers from that drawback. Also, many are expensive and do not lend themselves to automation.

Referring to FIG. 1E, another type of four-way valve is formed by interconnecting two tubes 937 and 938 with crossover lines 935 and 936. This design is disclosed in U.S. Pat. No. 6,189,388 (Hereafter, "U.S. Pat. No. '388"). Tube pinching actuators 941–944 are used to force fluid through different channels, depending on which actuators are closed. This device provides a hermetic seal and can be fairly inexpensive, but in a given configuration, significant no-flow areas are defined. These dead spaces can lead to the coagulation of blood, which is undesirable. Also, the interconnection of tubes in this does not lend itself to automated manufacturing.

The design of USP '388 provides an important benefit for sterile fluid lines. Because it has no seals which seal the external environment from the portions that are wetted by sterile fluids, there is no danger of contamination by infiltrating microorganisms or other contaminants. Also, the narrow spaces that attend the presence of seals—small gaps between movable parts and stationary parts—are places where fluid can stagnate, which can cause coagulation of some fluids or other adverse effects, depending on the fluid and application. The design of USP '388, however, does have the serious deficiency of providing very long lengths of tubing in which no flow will occur at any given time while in use. This can lead to stagnation.

There exists in the prior art a need for flow directing valves that combine the features of potentially low cost so that they can be replaced as part of a sterile package, no tendency to create stagnation regions where there is no flow, and the capability of providing a hermetic seal to the environment.

SUMMARY OF THE INVENTION

Briefly, A flow diverting appliance has a flexible valve body to which a number of flow lines are connected. The valve body is deformed to create different flow paths within it. The valve body may be deformed, for example, by pinching it to define press-seals in an enclosed volume inside the valve body. The press seals divide the enclosed volume to form exclusive flow channels which allow communication between some flow lines and permit flow communication between other lines. The invention provides a way of making flow diverters part of a replaceable blood circuit which is fully hermetic and with no dead-end spaces which would allow blood to coagulate.

The valve body may be incorporated in a disposable fluid line for use in extracorporeal blood processing equipment. The valve body may be made integral with multiple flow lines and may define a Y-shaped flow selector, a four-way valve, or other possible configurations. When deformed by actuators, the valve body assumes one of multiple configurations, each defining one or more selectable flow passages. By deforming the valve body, fluid can be made to reverse flow direction or be directed along selected paths.

Portions of the valve body may be made from a flexible polymer such as polyvinylchloride (PVC). The operating temperature and gauge pressure impose constraints on the material thickness, shape, and other features. In a preferred embodiment of a four-way valve, a cylindrical section is ultrasonically sealed around a pair of tubes inserted at each open end forming a sealed bladder. In this embodiment, the material, for example, PVC, has a high degree of resilience and assumes a pillow shape even in the presence of a negative gauge pressure. This structure forms the valve body, which is pinched by anvils to form a seal in the center of the bladder. Two anvils are used. One pinches the bladder in one direction to form a pair of parallel channels uniting two pairs of the four lines and the other pinches it in a perpendicular direction to form a pair of U-shaped channels uniting two other pairs of the four lines.

In another embodiment of a four-way valve, an injection-molded cross of flexible material is connected to four lines. The actuator anvils pinch the cross at respective diagonal angles cutting it into respective sets of right-angle conduits to join the respective lines. In a Y-shaped flow diverter, three lines are inserted in a cylinder of ultrasonically weldable polymer and sealed to a bladder. To actuate this embodiment, anvils selectively cut off one of the lines by pinching the bladder.

In other embodiments, the bladder may be made thinner-walled and held open by means other than the strength and resilience of the material. For example, engagement devices may be provided on the outside of a bladder which are pulled apart by the actuator. Alternatively, in addition to anvils, the actuator may be provided with supports which squeeze or support parts of the valve body from the sides to keep it from collapsing.

In another aspect of the invention, where two anvils are used, the anvils are arranged on opposite sides of the valve body. One is urged by a spring and the other is urged by a solenoid. When the solenoid is activated, the solenoid-urged anvil pushes the spring-urged anvil back away from the valve so that only former deforms the valve body. When the solenoid is released, the spring-urged anvil pushes the solenoid-urged anvil back so that only the spring-urged anvil deforms the valve body. In this way, the device can be actuated with only one active actuator mechanism. Note that although the discussion contemplates a solenoid, the actuator could employ any suitable device, for example, a screw-driven linear actuator, a hydraulic or pneumatic actuator, or other compatible mechanism.

In all of the above embodiments, no significant dead spaces occur in the running lines, as distinguished from prior art valves. Also, the structure of the valve body lends itself to incorporation in fully premanufactured and sterilized fluid lines. In addition, the actuator mechanism is simple and requires few moving parts.

The avoidance of dead spaces requires that a bulk flow be such as to insure that all fluid in a region is moving. This can be insured by designing the flow regions in such a way as to insure that the length scale of the flow channel cross-section is not much smaller than any channel dead ends. That is, the channel length where no flow occurs should not be much greater than its diameter, including an inlet transition. This insures that momentum is transferred to the fluid in these areas to prevent stagnation of flow. This transfer can happen as a result of viscous diffusion of momentum or turbulent diffusion of momentum. If the flow is rapid enough or the diameters large enough (i.e., high Reynolds number), turbulent diffusion can reach multiple diameters into dead end channels. In medical applications, it is considered impractical to provide flow channels with a high degree of turbulent energy and so the design constraint is to insure that the dead end channels are no more than one or two diameters in length. Clearly this is not the case with USP '388.

The invention will be described in connection with certain preferred embodiments, with reference to the following illustrative figures so that it may be more fully understood. With reference to the figures, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

BRIEF DESCRIPTION OF THE DRAWINGS

FIG. 2A is a front view of a four-way valve body according to an embodiment of the invention.

FIG. 2B is a side section view of a four-way valve body and actuator components according to the embodiment of FIG. 2A.

FIGS. 13A–13D illustrate the configuration of the valve body of FIGS. 12A–12C by an actuator mechanism according to an embodiment of the invention.

FIGS. 18F–18H illustrate an embodiment of the actuator mechanism of FIGS. 18–18C in one of two possible actuated configurations.

FIG. 19C illustrates a variation on the valve body of FIGS. 19A–19B.

FIGS. 20A and 20B illustrate front and section views of a mechanism for actuating and externally supporting a flexible valve body to prevent collapse under negative pressure.

DETAILED DESCRIPTION OF THE PREFERRED EMBODIMENTS

Figure 1:
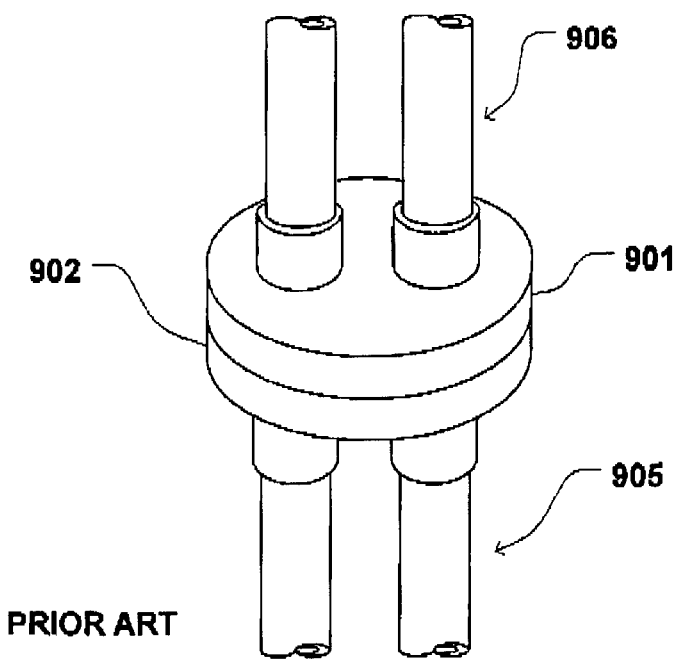
FIGS. 1A–1D1, 1D2, and 1E illustrate various valves according to the prior art.
Figure 1B:
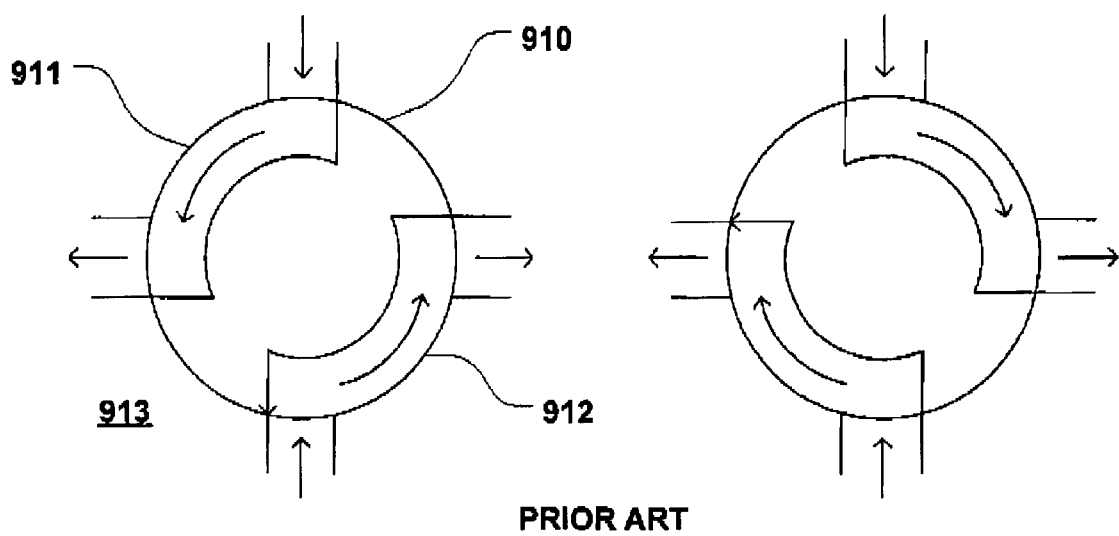
Figure 1E:
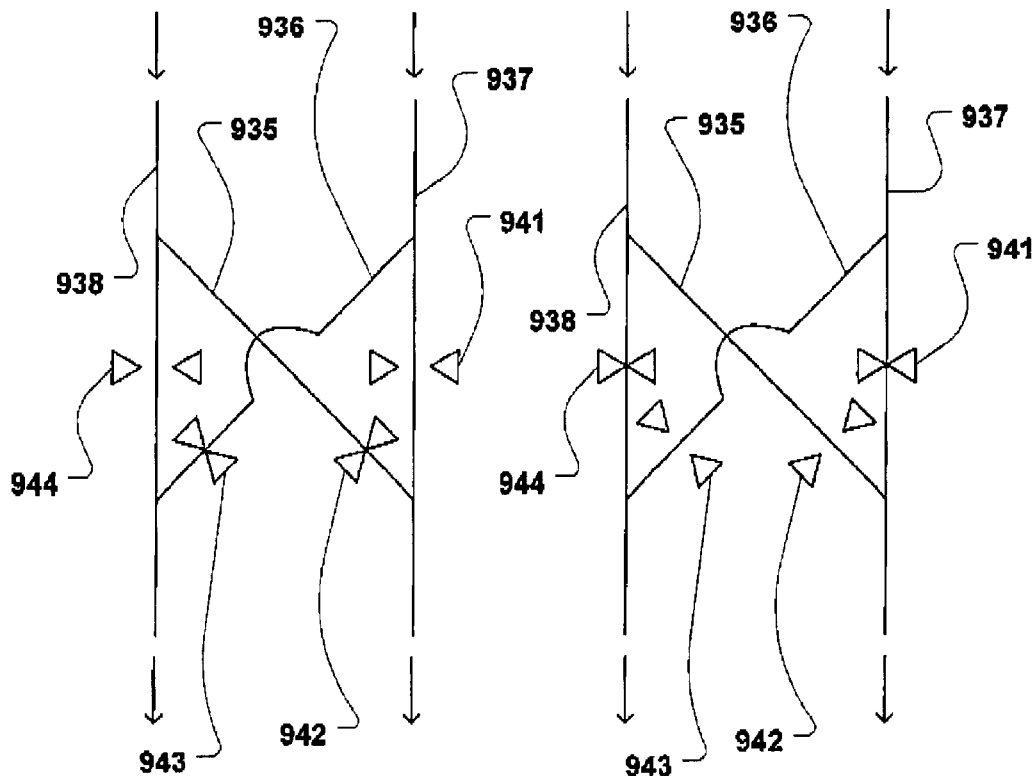
Figure 2:
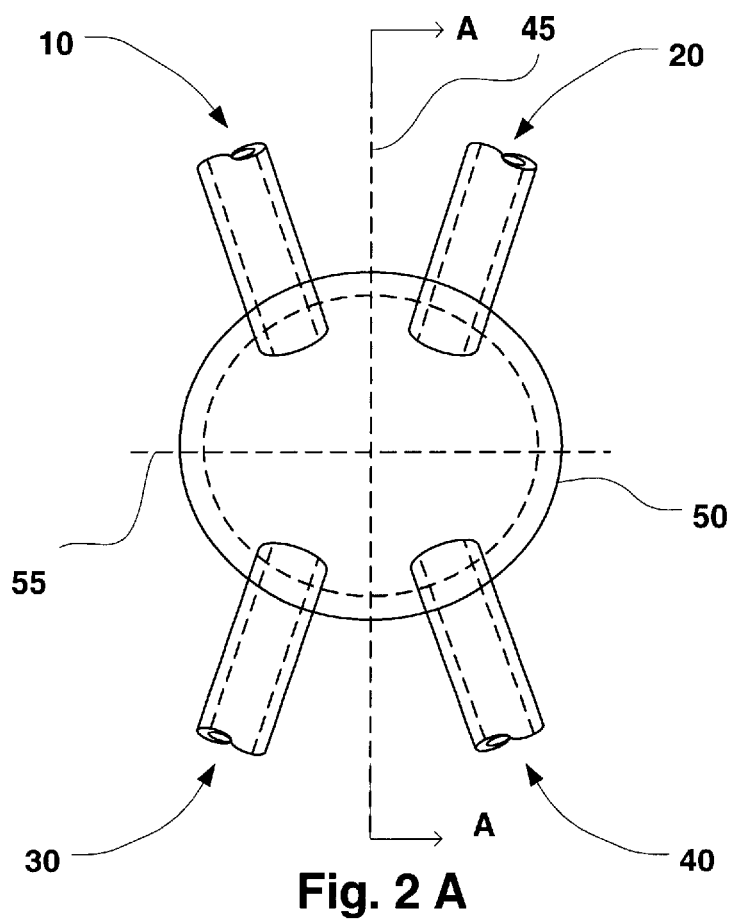
Figure 2:
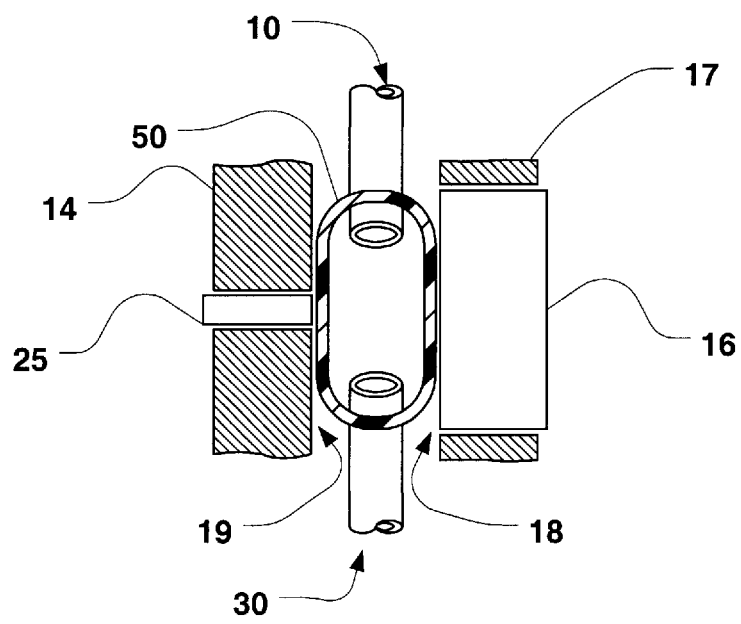

Referring now to FIG. 2A, is a figurative representation of a flexible valve body 50 with ports 10, 20, 30, and 40. The valve body allows flow from any channel 10–40 to flow to any other channel 10–40. According to the invention, the valve body is pinched along a line, such as the lines 45 and 55, to reshape the valve body 50 such that each channel is in flow communication with only one other. Thus, if the valve body 50 is pinched along the line 45, fluid can flow between port 20 and port 40 and between port 10 and port 30. If the valve body 50 is pinched along the line 55, fluid can flow between port 10 and port 20 and between port 30 and port 40.

Figure 5A:
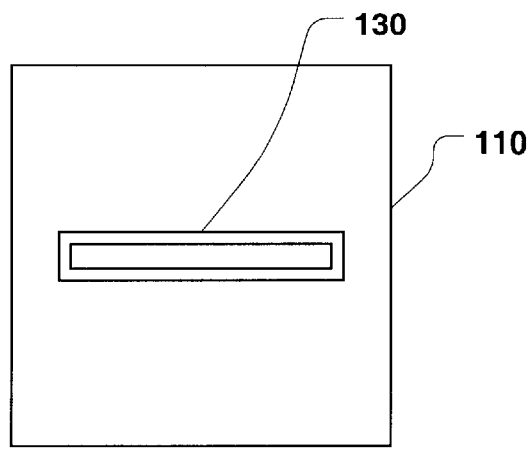
FIG. 5A is a front view of a first half of an actuator mechanism for a four-way valve according to an embodiment of the invention.
Figure 5B:
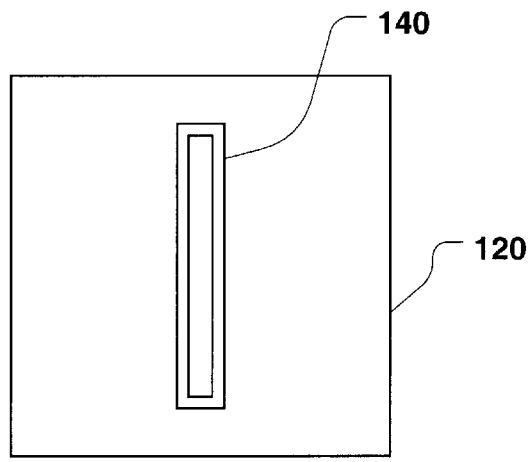
FIG. 5B is a front view of a second half of an actuator mechanism for a four-way valve according to the embodiment of FIG. 5A.

Referring now to FIG. 2B, a section view taken in a plane coinciding with either of the lines 45 and 55 and perpendicular to the plane of FIG. 2A shows the valve body 50 in section. On either side of the valve body (and not shown in FIG. 2A) are actuators 18 and 19. Each actuator has a respective anvil 25, 16 and a table 14, 17, with the table 14, 17 surrounding a respective anvil 25, 16. Refer momentarily to FIGS. 5A and 5B, which show how the tables 14 and 17 and anvils 25 and 16 look as viewed from their fronts facing the valve body 50. The table 14 corresponds to the table 110 and the table 17 to the table 120. The anvils 25 and 16 correspond to the anvils 130 and 140.

Figure 3A:
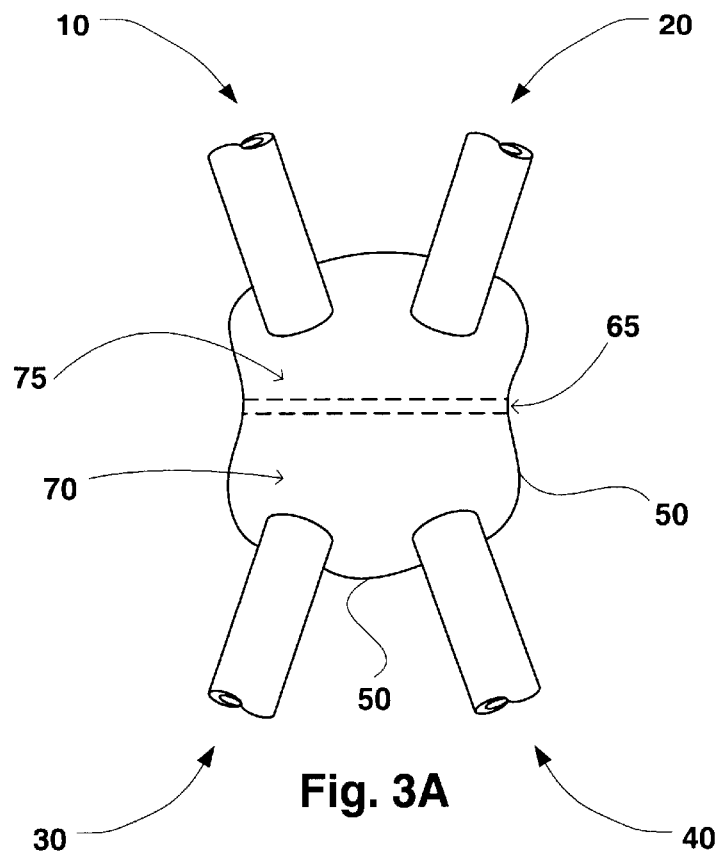
FIG. 3A is a front view of the valve body of FIGS. 2A and 2B in a first configuration caused by pinching the valve body.
Figure 3B:
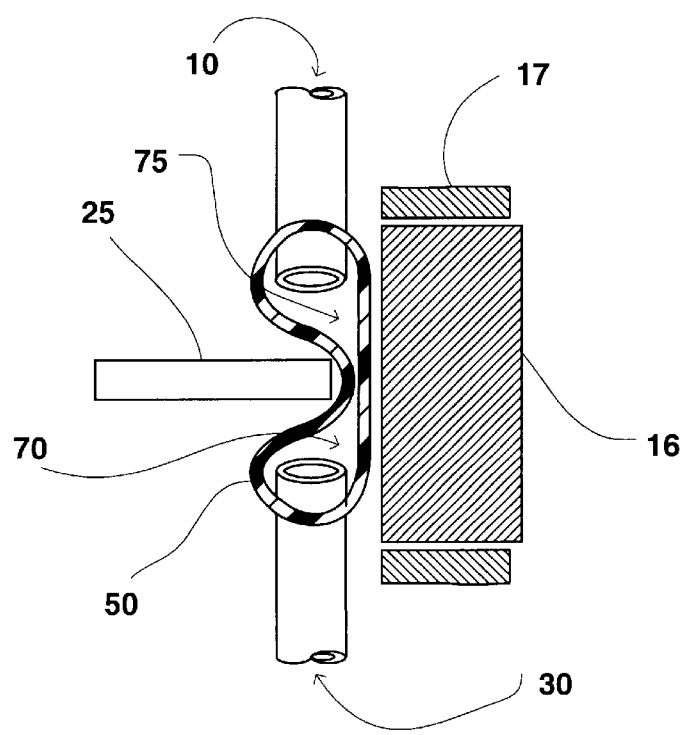
FIGS. 3B and 3C showing side and top section views, respectively, of the configuration of FIG. 3 with actuators.
Figure 3C:
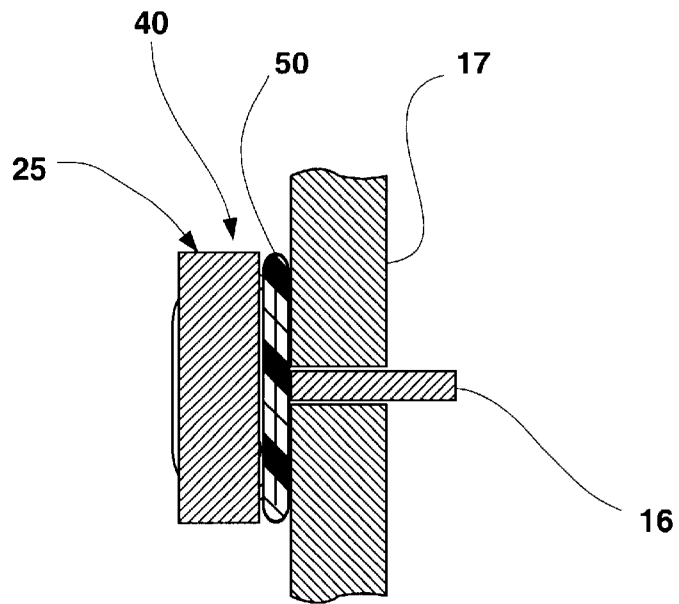

Referring now to FIGS. 2B and 3A, when the actuator 19 is activated, the anvil 25 moves forward relative to the table 14 surrounding it so that it pinches the valve body 50 along the area 65. Referring to FIGS. 3B and 3C, the valve body 50, pinched as illustrated, causes two flow channels 70 and 75 to be defined. The flow channel 70 permits flow communication between the ports 30 and 40 and the flow channel 75 permits flow communication between the ports 10 and 20. Flow is either not permitted, or much more restricted, between other pairs of ports. As can be seen, the table 17 helps to support the valve body 50 when the anvil 25 is pressed against the valve body 50. Also, the opposing anvil 16 at a 90 degree angle with respect to the anvil 25 also helps to support the valve body against the anvil 25. Preferably, the table 17 and the anvil 16 form a smooth continuous surface that supports the valve body 50.

As illustrated, the pinch results in a 100% seal between the flow channels 70 and 75, but this is not necessarily required. It depends on the application. For example, in some applications, leakage across the area 65 would result in some flow short-circuiting, but some may be acceptable.

Figure 4A:
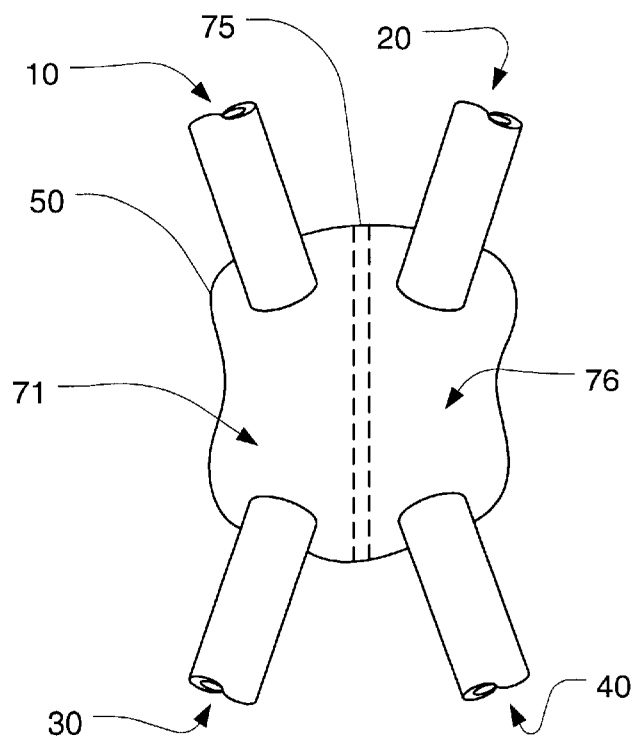
FIG. 4A is a front view of the valve body of FIGS. 2A and 2B in a second configuration caused by pinching the valve body along a different axis.
Figure 4B:
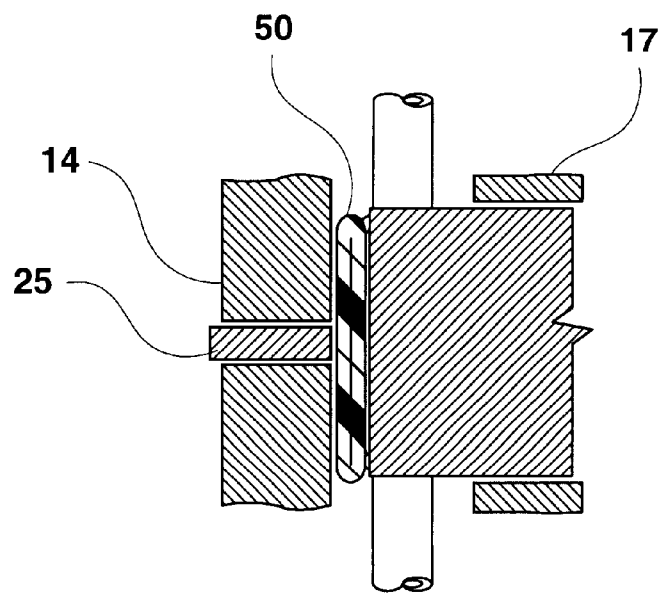
FIGS. 4B and 4C showing side and top section views, respectively, of the configuration of FIG. 5 with actuators.
Figure 4C:
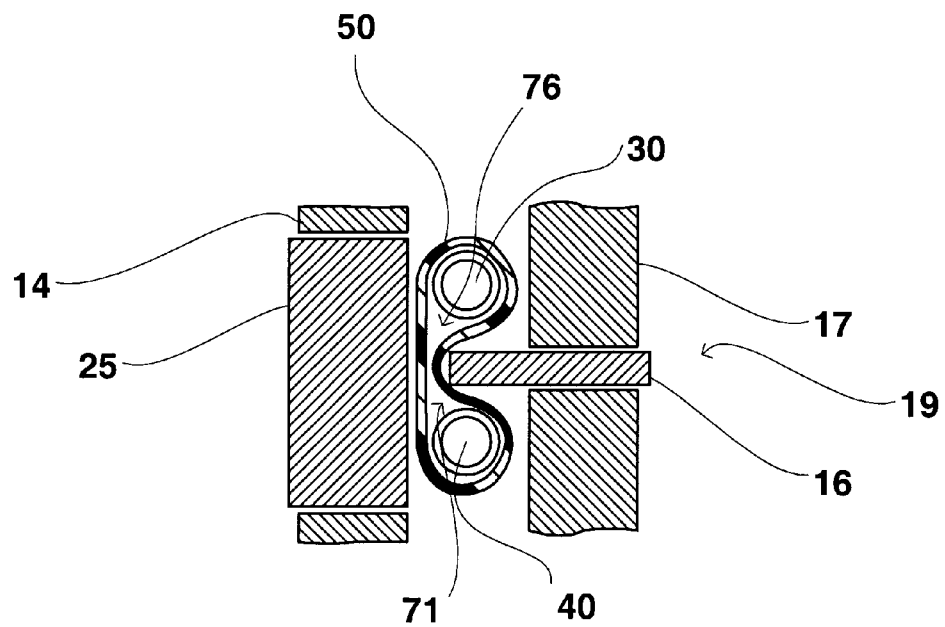

Referring now to FIGS. 2B and 4A, when the actuator 18 is activated, the anvil 16 moves forward relative to the table 17 surrounding it so that it pinches the valve body 50 along the area 75. Referring now also to FIGS. 4B and 4C, the valve body 50, pinched as illustrated, causes two flow channels 71 and 76 to be defined. The flow channel 71 permits flow communication between the ports 10 and 30 and the flow channel 76 permits flow communication between the ports 20 and 40. Flow is either not permitted, or much more restricted, between other pairs of ports. Again, the table 14 and the anvil 25 help to support the valve body 50 when the anvil 16 is pressed against the valve body 50 and, preferably, form a smooth continuous surface that supports the valve body 50.

Note the fact that the flow channels 70, 75 and 71, 76 have no significant dead flow areas. When fluid flows through them at a significant rate, stagnation is unlikely because the size of the flow channel is not changed dramatically and, so long as the mass flow is sufficient, any mean flow deceleration will generate enough turbulence to insure that volume of the flow channels is 70, 75 and 71, 76 does not cause precipitation of suspended material, or coagulation. Preferably, the size of the flow channels 70, 75 and 71, 76 is such that the mean flow velocity transition (i.e., the change in mean flow velocity) through the flow channels 70, 75 and 71, 76 is not great or nonexistent (i.e., constant flow area—i.e., approximately the same as through the ports 10, 20, 30, and 40) with preferably constant hydraulic diameter) and or the mass flow is sufficiently high to insure that stagnant volumes do not arise.

The conditions for preventing flow stagnation vary from one system to another and depend on the fluid, the sizes of the channels and mean flowrate (e.g., Reynolds number of the flow), and even the history of the flow for non-Newtonian fluids and suspensions. But various techniques will help to insure that flow does not stagnate. Providing a constant hydraulic diameter of a flow path will insure no flow reversal takes place and uniform distribution of momentum by viscosity or its turbulent analog. Also, the removal of dead-ends, or at least minimizing their size so that they are not long, for example, no longer than they are deep, will insure that flow is not completely stagnant within them. In U.S. Pat. No. 6,189,388, for example, the latter issue is not addressed by the design. Also, designing the device so that no fluid is cut off in an isolated space will help to insure fluid does not stagnate.

In the generic valve body 50 of the foregoing figures, flow channels are generally assured of having no dead ends spaces so long as the wetted surface to volume ratio of the valve body 50, and any projecting volumes in communication with it, is kept low. By "projecting volume," we refer to a volume, for example a small recess associated with a mechanical seal or a dead-end flow channel, which does not have a mean flow in it. Another way to state it is that the wetted surface of the valve body 50 should have no projections with a high aspect ratio and no mean flow. For low flow rates, the aspect ratio ratio should be no higher than required to transport momentum from a moving flow by viscous diffusion. An aspect ratio of about 2 or less would insure that there was some movement driven by viscous flow.

If the mean flow is characterized by significant turbulence, then the absolute dimensions of the volume projection relative to the scale of the channel conveying the mean flow must be taken into account. If a volume projection has absolute dimensions that are significantly smaller than the length scale of the mean flow (usually the maximum diameter of the flow channel), then there will be no significant vorticity ("vortical motion" or "vorticity" being terms of art in fluid mechanics that refer to the local transient eddy structures that make up turbulent fluid motion whose size or "scale" can be measured and predicted in a statistical sense) at the scale of the volume projection. In other words, turbulence cannot transfer momentum into tight spaces because viscosity dissipates the turbulent energy at small scale. Certainly in blood flow applications this would have to be taken into account.

In the above example, the valve body 50 is topologically congruent with a sphere, but need not be to satisfy the above requirement. For example, see FIGS. 14A–14C and the attending discussion, where the valve body is topologically congruent with a torus. A topological sphere almost guarantees that there will be no dead flow regions formed when the valve body is deformed to define selected flow channels, and so is preferred in some applications such as extracorporeal blood circuits. There can be advantages, however, to a toroidal valve body, such as resistance to collapse under negative gauge pressure, although the problem of dead-end channels may place design constraints in blood circuits.

Figure 6:
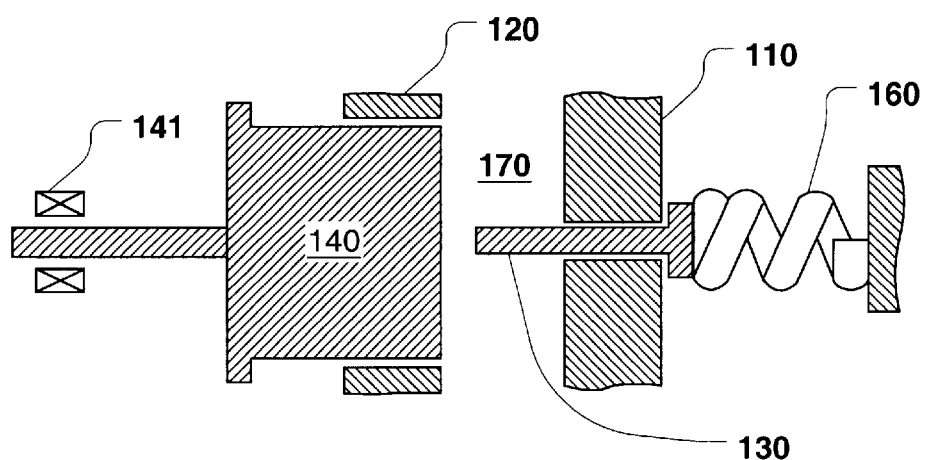
FIG. 6 is section view of the embodiment of FIGS. 5A and 5B.

Referring now to FIG. 6, with the opposing relationship between the anvils as illustrated in the foregoing figures, it is possible to arrange for only one active actuator to switch between the configuration of FIGS. 3A–2C and that of FIGS. 4A–4C. A spring 160 forces one anvil 130 forward so that it will press a valve body in front of it when an opposing anvil 140, moved by a linear actuator, for example a solenoid 141, is retracted. As should be readily apparent from FIG. 6, when one anvil 130, 140 moves forward, it will push the other back through anything placed between them. In one case, the valve body 50 would be forced back. The solenoid could be replaced with any suitable actuator, for example, a screw-driven linear actuator, a hydraulic or pneumatic actuator, or other device.

It is apparent that the valve body 50 can be deformed by a wide variety of different mechanisms to form selected channels within it. The one illustrated in the foregoing figures is only an example. Also, the shape of the valve body 50 can be a variety of different shapes and still achieve the functionality discussed above, as is readily apparent.

Figure 7A:
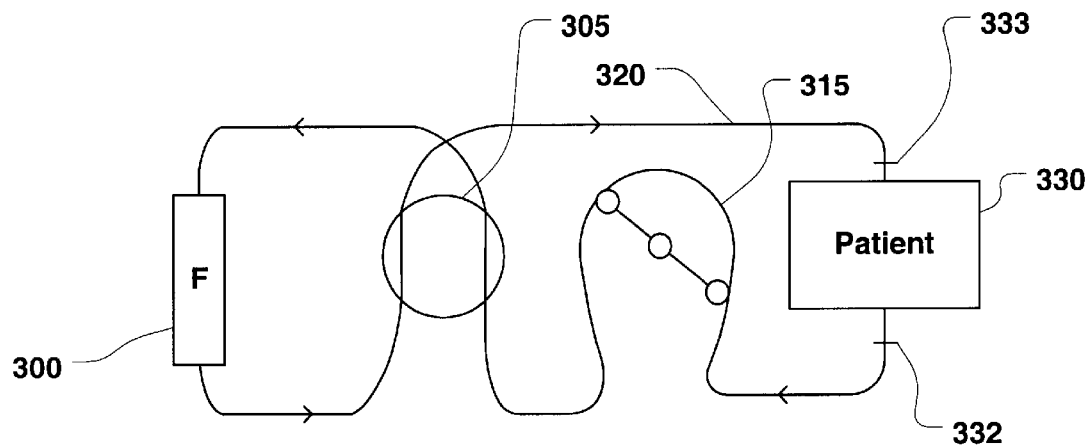
FIG. 7A shows a flow path for a blood treatment system with a four-way valve in a first configuration to illustrate an application of the present invention.
Figure 7B:
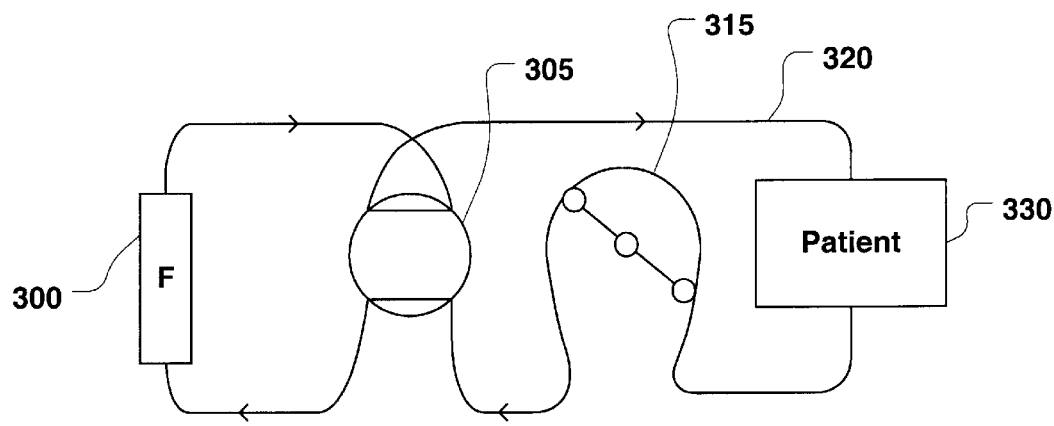
FIG. 7B shows the flow path of FIG. 7A with the four-way valve in a second configuration.

Referring now to FIGS. 7A and 7B, an example of an application for a four-way valve embodiment of the invention, such as shown in the foregoing figures, has a blood circuit 320. Blood is drawn from a patient 330 using suction generated by a pump 315 (typically a peristaltic pump) and conveyed to a four-way valve 305. From the four-way valve, blood is sent to either of two ends of a filter 300, depending on the configuration of the four-way valve 305. Note that the four-way valve 305 is represented in the figure symbolically showing two possible paths the blood can take based on the configuration, with blood taking U-shaped paths in FIG. 7B and parallel paths in FIG. 7A. The filter 300 is intended to represent any type of treatment process, for example, dialysis or hemofiltration.

As described in the commonly assigned copending U.S. patent application entitled DEVICE AND METHOD FOR ENHANCING PERFORMANCE OF MEMBRANES, which is hereby incorporated by reference as if set forth in its entirety herein, reversing the flow of blood through filter provides certain benefits. The actuator mechanism of FIGS. 5A, 5B, and 6 may be incorporated in a machine designed to accept the blood line 320. For example, such machines normally incorporate the motor part of a peristaltic pump, as figuratively illustrated at 315. When the blood line 320 is installed in such a device, such an actuator would engage the four-way valve 305 and operate it. According to the teachings of the application incorporated by reference above, the actuation may be automated and flow through the filter 300 reversed repeatedly and automatically during treatment.

In many systems for extracorporeal blood treatment, a hermetic blood line is employed. Such lines are manufactured joints connected and sealed, and sterilized as a unit. They are used once and then discarded. This minimizes setup complexity and helps to insure sterility. One benefit of the valve design of the invention is that it can be incorporated in a blood line that is preconnected and sealed from end to end. The ends may be only those 332 and 333 connecting to the patient 330 (via an access—not shown). In some cases, the filter 300 may be a separate part from the blood line 320 with connectors (not shown) provided to make the connection to the blood line 320 in the field. The four-way valve 305, however, can be built into the blood line 320 forming a completely hermetic unit with no seals in the four-way valve 305 that could compromise sterility. Note that the blood line 320 can be manufactured with only the valve body included in the sealed blood line. Note also that the valve body can be a simple and inexpensive component, as should be apparent from the foregoing description with reference to FIGS. 2A–2B, 3A–3C, and 4A–4C and additional ones to follow. Thus, the design may lend itself also to incorporation in a low cost premanufactured blood line 320.

Figure 8A:
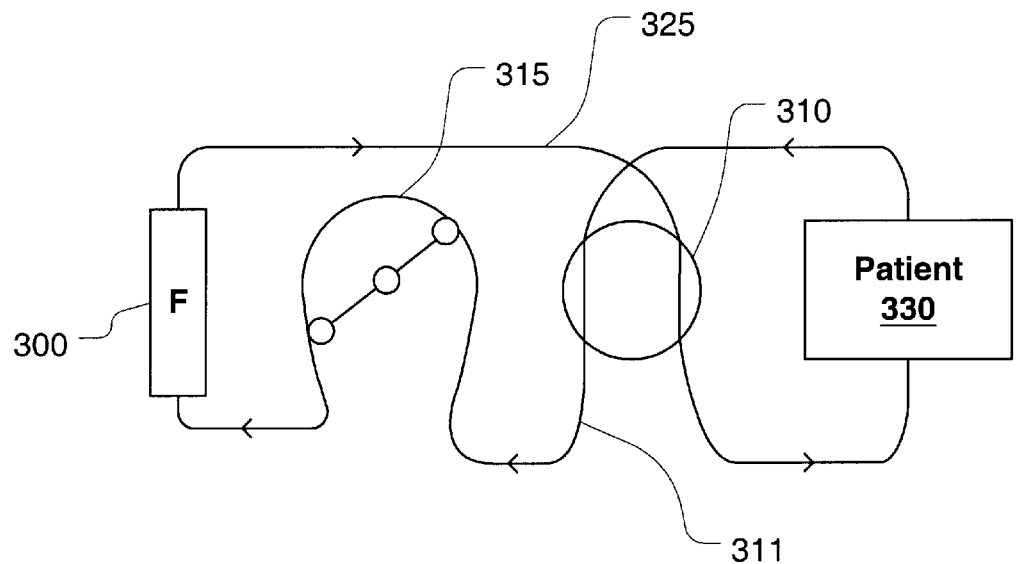
FIG. 8A shows another flow path for a blood treatment system with a four-way valve in a first configuration to illustrate another application of the present invention.
Figure 8B:
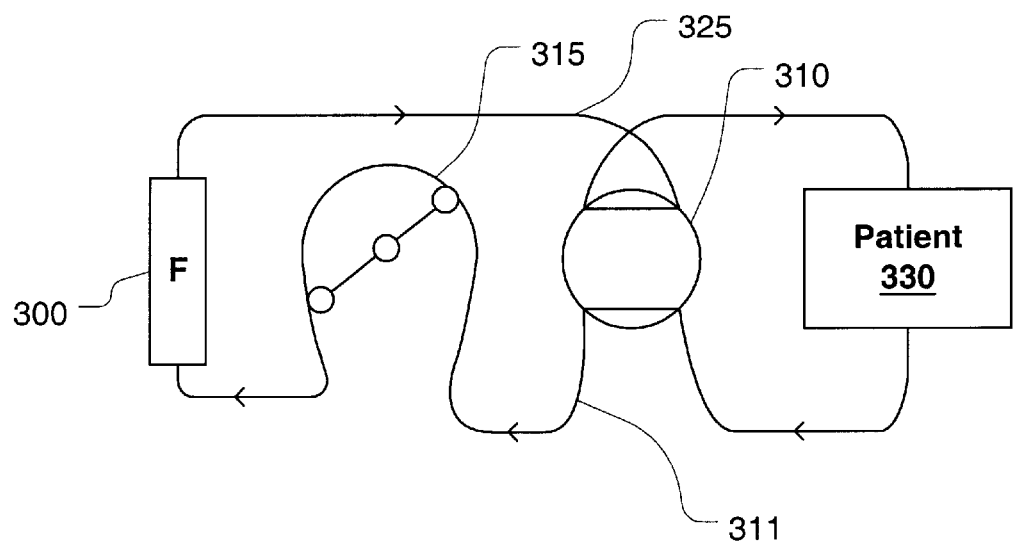
FIG. 8B shows the flow path of FIG. 8A with the four-way valve in a second configuration.

Referring now to FIGS. 8A and 8B, a blood line 325, similar in respects to that of FIGS. 7A and 7B, provides for blood flow from a patient 330 through a four-way valve 310, pump 315, and a filter 300. In this application, the flow of blood through the lines linking to the patient 330 may be reversed via the four-way valve 310. As described in the commonly assigned copending U.S. patent application entitled METHOD AND APPARATUS FOR LEAK DETECTION IN A FLUID LINE, which is hereby incorporated by reference as if set forth in its entirety herein, reversing the flow of blood through the patient may provide certain benefits such as an ability to clear obstructions from the patient access or leak detection. Again, as discussed with respect to the application of FIGS. 7A and 7B, an actuator may be operated repeatedly during a treatment cycle.

Figure 9:
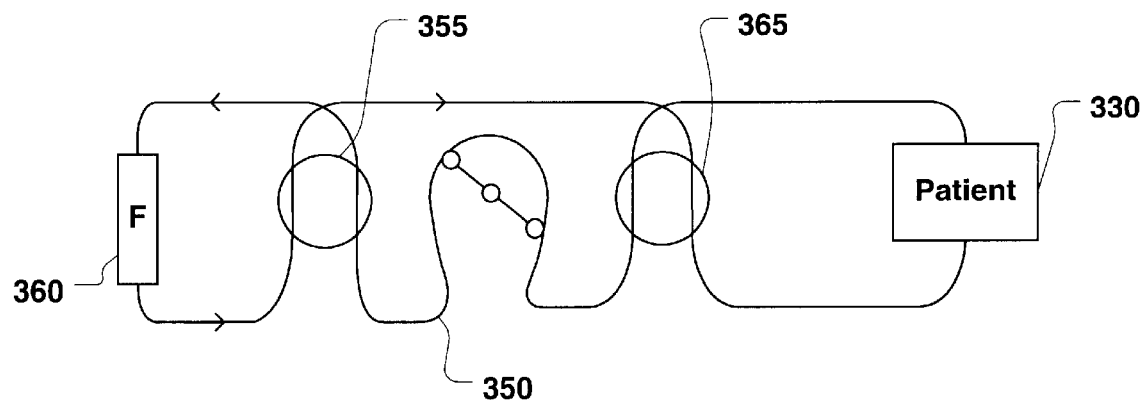
FIG. 9 shows yet another application of a four-way valve according to an embodiment of the invention.

Referring to FIG. 9, another application example for a four-way valve built in accordance with the invention is shown. In a blood line 350, two four-way valves 355 and 365 perform the functions of four-way valves 305 and 310, respectively, of FIGS. 7A, 7B, 8A, and 8B. In this application, the flow through the filter 360 and that through the patient 330 may be changed independently. This allows for the switching of filter flow direction to occur on a different schedule from that for patient flow direction. As taught by the applications incorporated by reference above, the switching of patient flow direction may need to be done more frequently or less frequently than that for filter flow direction. Also, as taught by the prior art, the other purposes for flow reversal may indicate differing schedules for the flow reversal, for example, one may be manually triggered while the other may be automatically triggered.

Figure 10A:
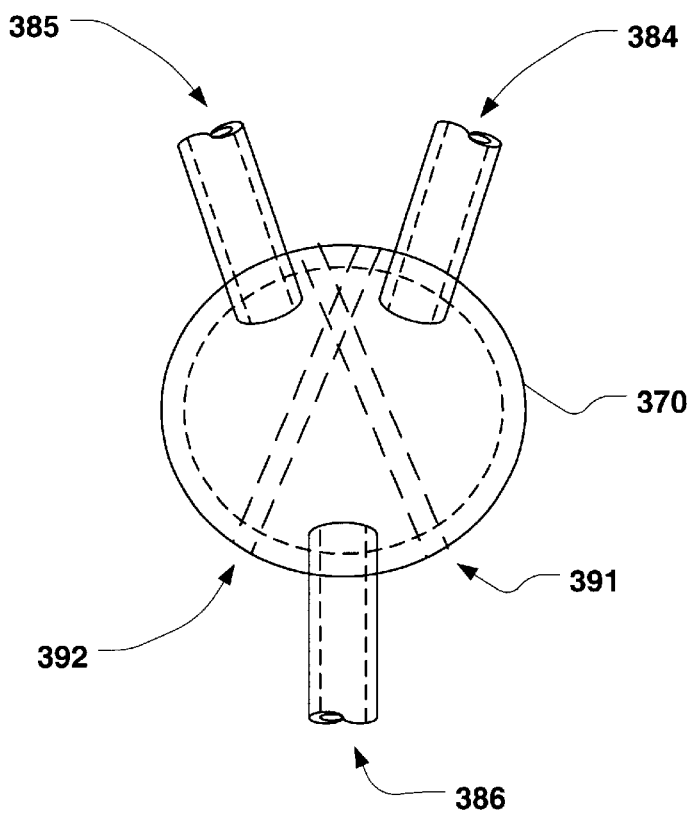
FIG. 10A is a flow diverter valve according to an embodiment of the invention.

Referring now to FIG. 10A, the inventive device is adaptable to a number of different flow diverting embodiments. Another example is a flow switch 370, in which an inlet or outlet 386 may be selectively joined to one of two outlets or inlets 385 and 384. That is, in one configuration, depending on the flow direction, a single outlet 386 can be selectively connected to one of two inlets 384 and 385. Alternatively, for the opposite flow direction, a single inlet 386 is selectively connected to one of two outlets 384 and 385. Here, anvils are pressed against a valve body 370 to seal (or at least partly seal) areas 391 and 392. When flow is to pass between port 384 and 386, the area 392 is sealed by pressing an anvil (not shown). When flow is to pass between port 385 and 386, the area 391 is sealed by pressing the anvil.

Figure 10B:
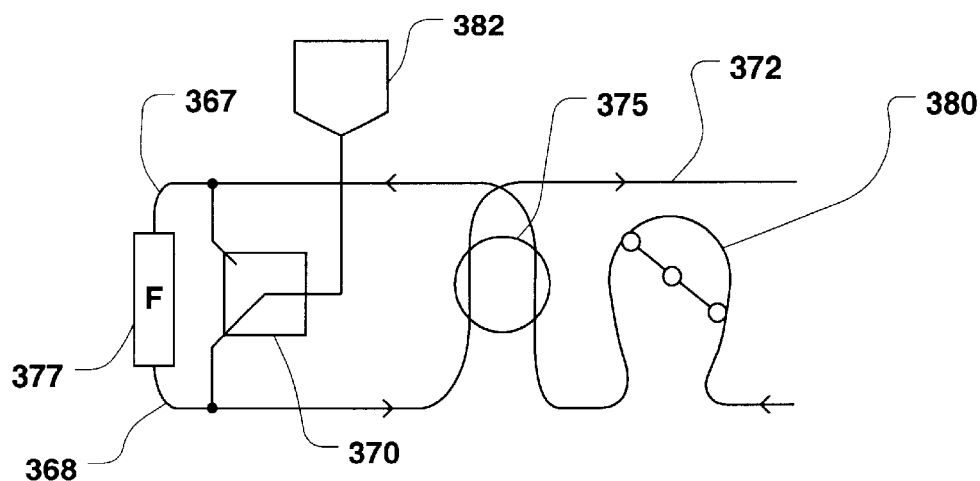
FIGS. 10B and 10C illustrate a flow director valve application according to an embodiment of the invention with the flow director valve in first and second positions, respectively.
Figure 10C:
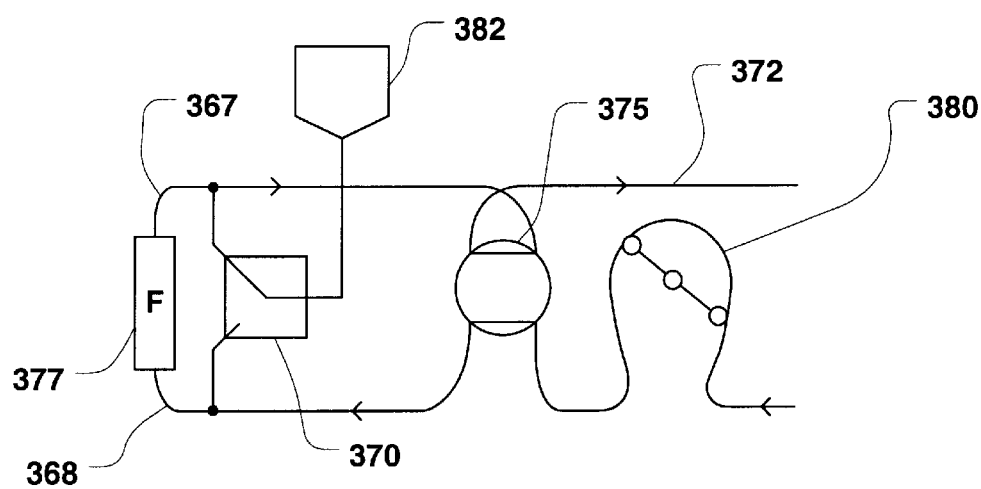

Referring to FIGS. 10B and 10C, an example of application for a flow diverter 370, such as shown in FIG. 10A, is the switching over of the flow of replacement fluid, from a reservoir 382, between lines 367 and 368 depending on a direction of flow of blood through a filter 377. In the application of FIGS. 10B and 10C, blood is driven through a blood line 372 by a pump 380. The blood line 372 has a four-way valve 375 that periodically switches a direction of flow of blood through the filter 377 during a treatment process as discussed with reference to FIGS. 7A and 7B. Generally, it is desired for replacement fluid to be supplied to the input end of the filter 377, for pre-dilution of the blood, or to the output end of the filter 377, for post-dilution. When the line through which blood is directed into the filter 377 changes in accord with the application of FIGS. 7A and 7B, to maintain the post-dilution or pre-dilution state, it is necessary to switch the flow of replacement fluid between lines 367 and 368. This function may be provided by the diverter 370.

Figure 11A:
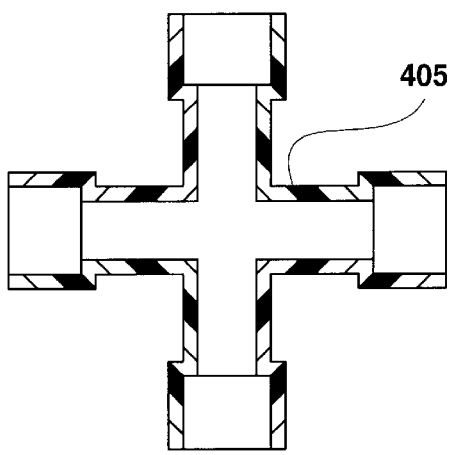
FIGS. 11A–11C illustrate an alternative design for a valve body according to an embodiment of the invention.
Figure 11B:
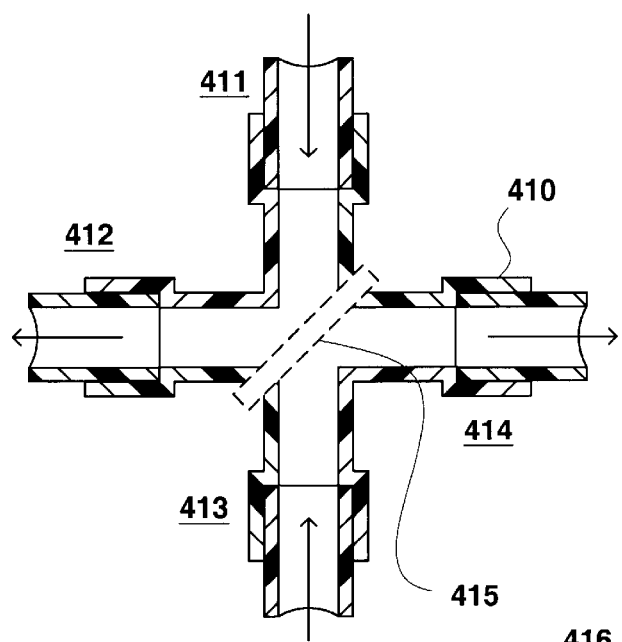
Figure 11C:
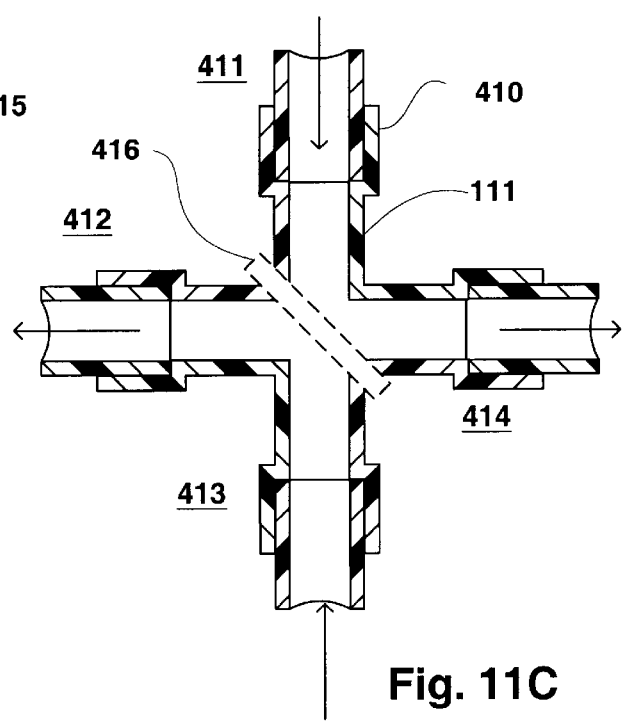

Referring now to FIGS. 11A–11C, a four-way valve body 405 may be formed of a compliant injection moldable polymer. The valve body 405 has four ports 411, 412, 413, and 414. Each port has a flanged portion, for example as indicated at 410, permitting tubing to be inserted and bonded to the valve body 405. Each port 411, 412, 413, and 414, may be selectively joined to either of two adjacent ports by forcing an anvil-edge 415, 416 against the center of the valve body 405 in one of two orthogonal directions as shown in FIGS. 11B and 11C. In FIG. 11B, the anvil-edge is pressed in a first direction joining ports 411 and 412 and simultaneously joining ports 413 and 414. In FIG. 11C, the anvil-edge is pressed in a second direction joining ports 411 and 414 and simultaneously joining ports 412 and 413. As can be seen by inspection, the flow passages form by pinching the valve body 405 are free of dead flow zones in both configurations.

Figure 12A:
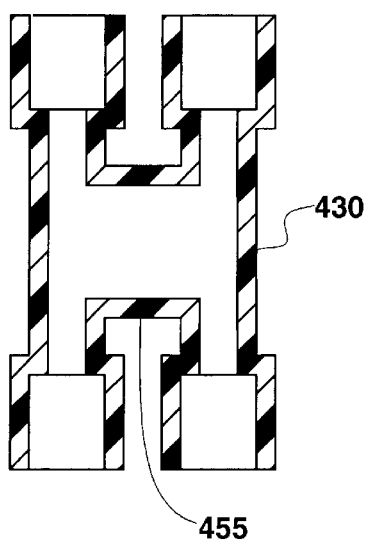
FIGS. 12A–12C illustrate an alternative design for a valve body according to another embodiment of the invention.
Figure 12B:
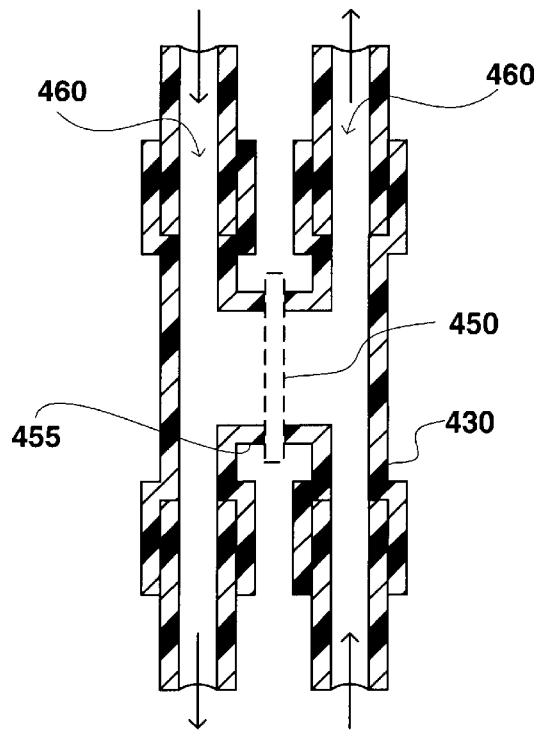
Figure 12C:
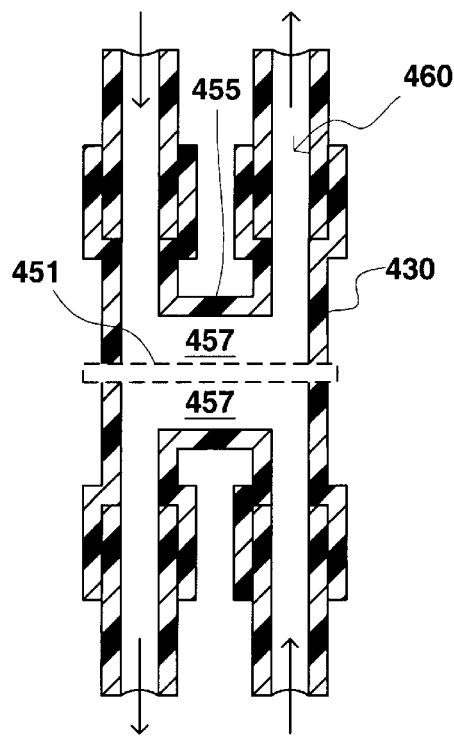

Referring now to FIGS. 12A–12C, in an alternative embodiment, a valve body 430 is formed in the shape of an "H." To form a first flow configuration (FIG. 12B), an anvil-edge 450 is perpendicular to the first orientation and pinches the bridge to bisect it and form two parallel channels 460. To form the second flow configuration (FIG. 12C), an anvil-edge 451 pinches the H-shaped bridge 455 longitudinally along the centerline of the crossing line 455 of the "H" to form mirror image U-shaped channels 457.

In the above four-way valve embodiments, the anvil edges 415, 416, 450, and 451 may be actuated by suitable linear actuators. Referring now to FIGS. 13A–13D, one way to control both orientations of the anvil edge 415, 416, 450, and 451 with a single solenoid is by disposing two perpendicular anvils 510 and 515 on opposite sides of the valve body 540. One anvil 515 may be urged toward the valve body 540 by a spring 550 while the other is forced by the solenoid 560. When the solenoid 560 is retracted, only the spring-urged anvil 515 deforms the valve body 540. When the solenoid 560 is extended, only the solenoid-forced anvil 510 deforms the valve body 540. Here, FIG. 13A shows the spring urged anvil 515 pressed along the bridge (parallel to the length of the bridge of the "H" as illustrated in FIG. 12C) as viewed from the side and FIG. 13B shows the same configuration as viewed from the top. FIG. 13C shows the solenoid urged anvil 510 pressed across and bisecting the bridge of the "H" (as illustrated in FIG. 12B) as viewed from the side and FIG. 13D shows the same configuration as viewed from the top. Support tables 520 and 525 provide support for parts of the valve body 540 that are not otherwise supported by the anvils 510 and 515.

Figure 14A:
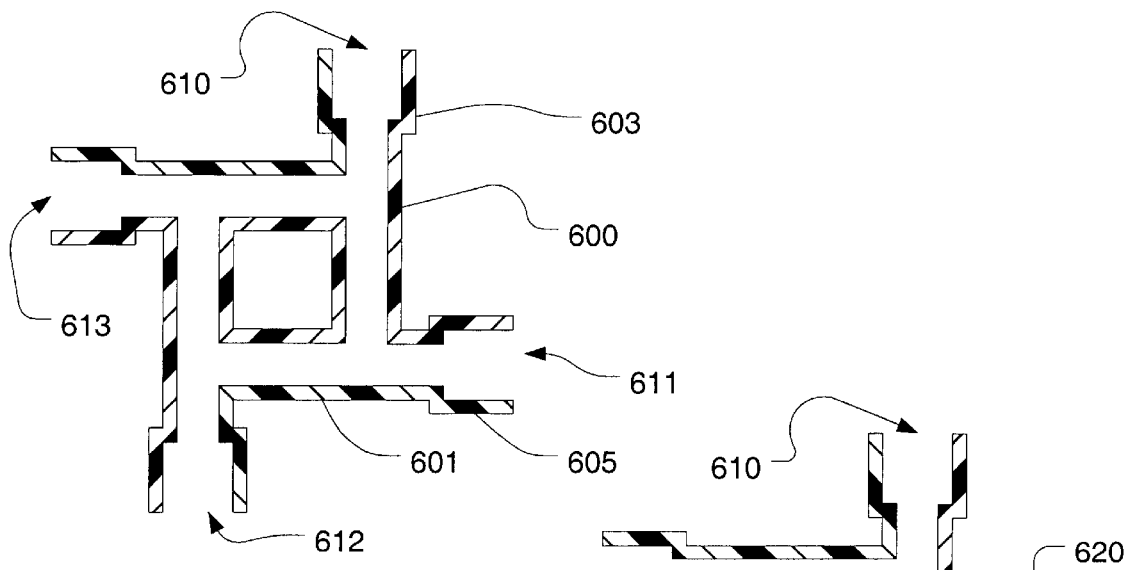
FIGS. 14A–14C illustrate an alternative design for a valve body according to yet another embodiment of the invention.
Figure 14B:
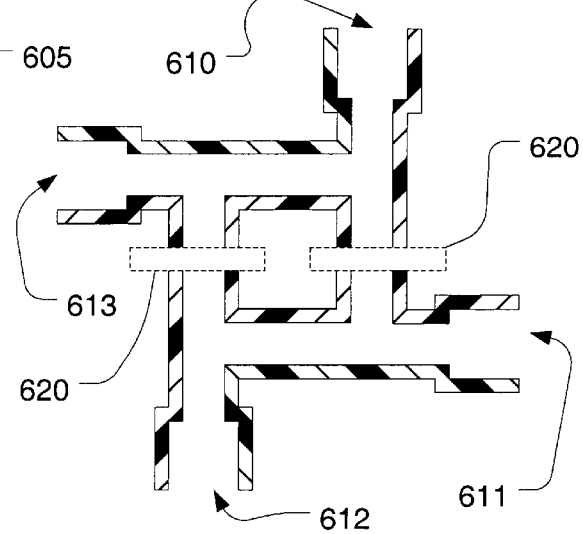
Figure 14C:
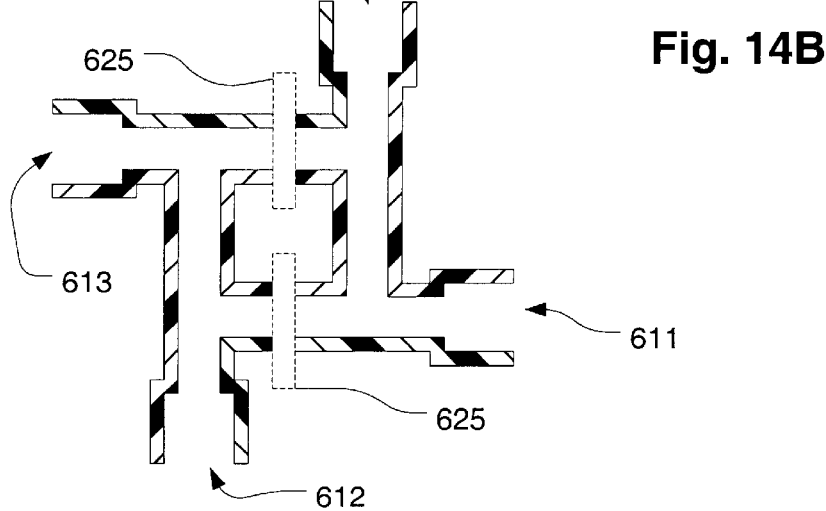

Referring now to FIGS. 14A, 14B, and 14C, another four-way valve body 600 embodiment is made up of intersecting cylindrical elements as indicated at 601. Each cylindrical element has a bonding collar 603 for receiving a tubing connection. As in previous embodiments, four ports are defined 610, 611, 612, and 613. To form a first flow configuration, the valve body 600 is pinched in the area indicated at 620. To form a second flow configuration, the valve body 600 is pinched in the area indicated at 625. In the first flow configuration, flow is possible between ports 610 and 613 and between 611 and 612. In the second flow configuration, flow is possible between ports 610 and 611 and between 612 and 613. The embodiment of FIGS. 14A–14C has the advantage of having flow paths with approximately cylindrical cross sections, which, because of the symmetry in the portions that are pinched, are more resistant to collapse under negative pressure, permitting softer materials to be used. Note the outlines 620 and 625 suggest two anvils edges are used on either side of the valve body 600, but it would be possible to use a single anvil edge.

Figure 15A:
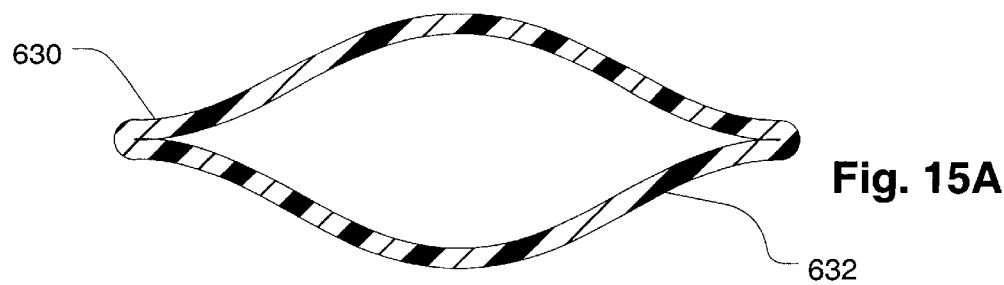
FIGS. 15A and 15B shows a design feature suitable for more rigid valve body configurations for purposes of discussion of the design of valve bodies for use in the invention.
Figure 15B:
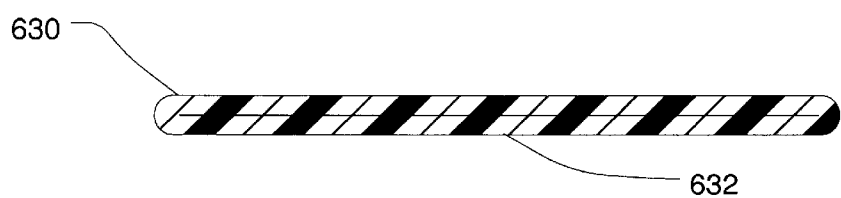

It should be clear from at least some of the applications discussed above that some parts of a four-way valve will experience a negative gauge pressure when they are in flow communication with a suction-side line. For example, referring back to FIGS. 8A and 8B, line 311, and a portion of four-way valve 310 are always under negative pressure during operation. This may place constraints on the construction and materials used for the valve body 50 (or the other embodiments, such as 387). Referring to FIG. 11A, in a purely positive-pressure application, the valve body 50/387 (and others discussed below) may be formed of very soft material. A soft material may be creased easily where the seal crosses the edges of the valve body. More rigid materials are preferably designed in such a way as to permit an effective seal without breaking. For example, as shown in FIGS. 15A and 15B, a valve body 632 is formed with a short radius bend 630 preformed in the body at the cross section that is destined to be pinched as shown in FIG. 15B to actuate the valve body 632. When the valve body 632 is pinched, the body does not have be greatly strained at the edges and so can be made of a stiffer material to resist collapse due to negative pressure. In addition, ribbing or other structural features can be incorporated in the valve body 632 to provide resistance to collapse.

Figure 16A:
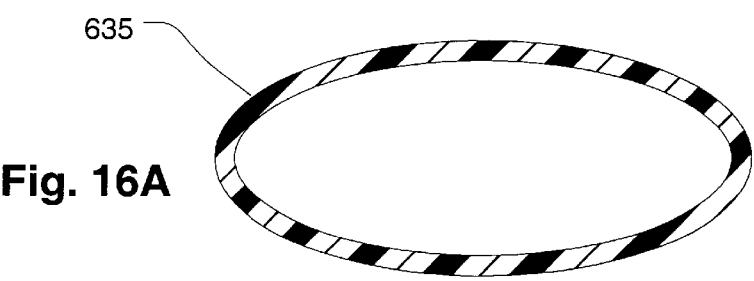
FIGS. 16A–16C discuss approaches for handling negative pressure with a highly compliant valve body.
Figure 16B:
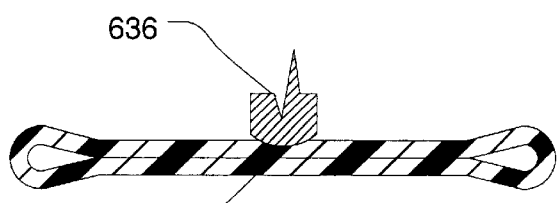
Figure 16C:
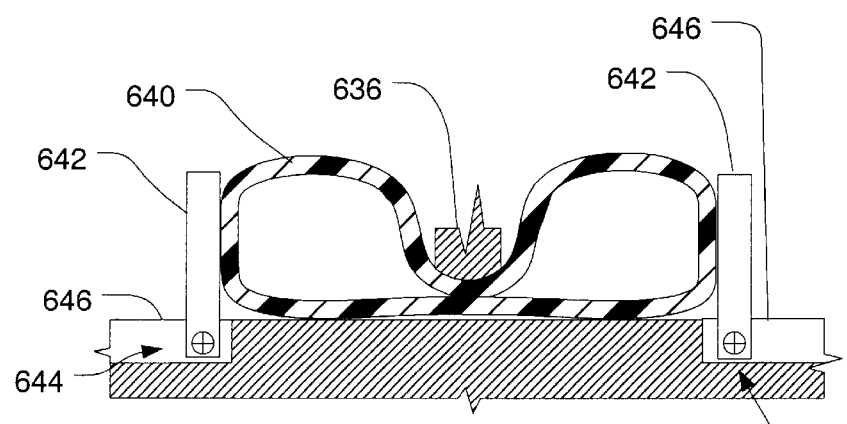
Figures 17A, 17B:
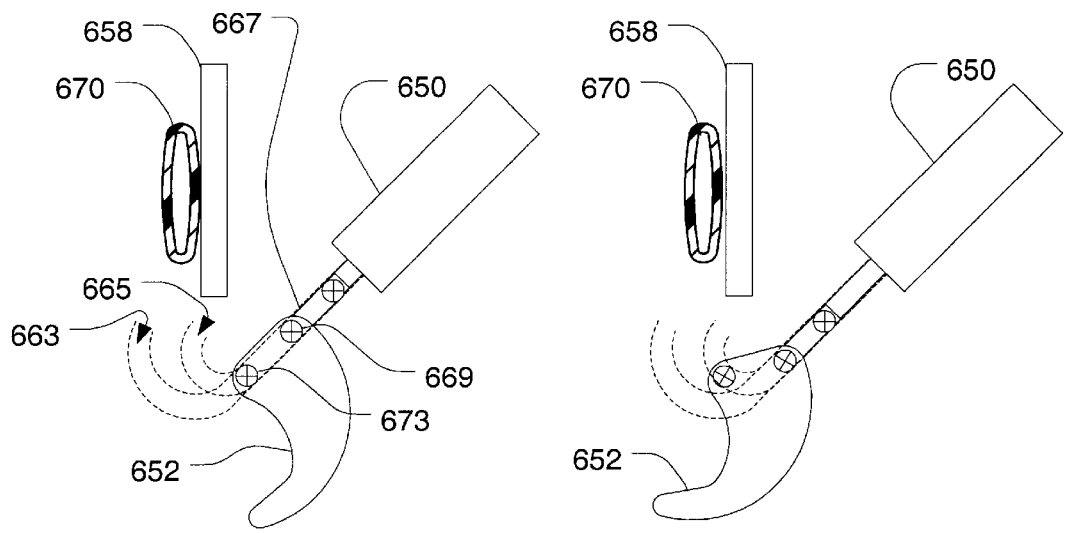
FIGS. 17A–17D are a sequence of side views of an alternative actuator mechanism that may be used in connection with various embodiments of the invention.
Figures 17C, 17D:
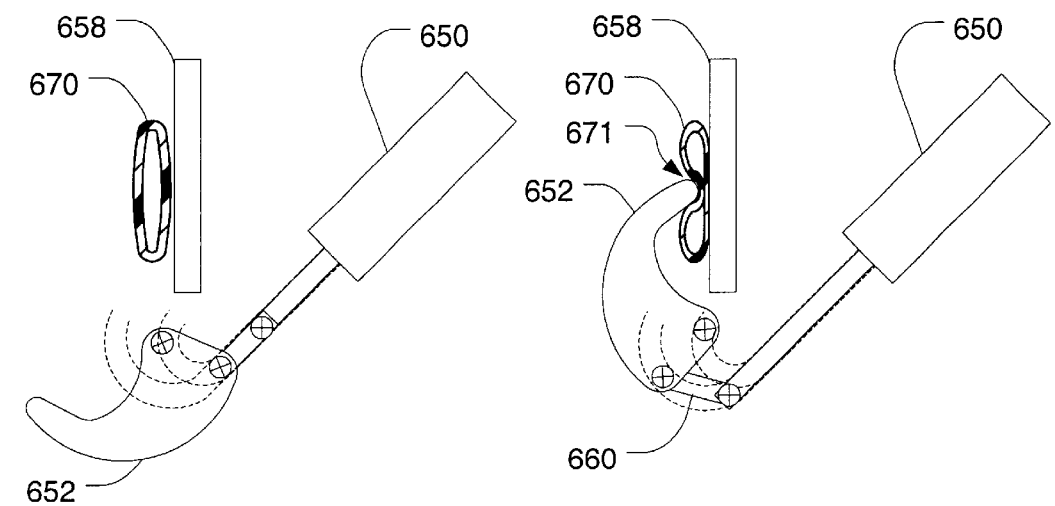

Another alternative is to employ an actuator mechanism that helps to keep the valve body from collapsing. For Example, in FIG. 16A, a soft round section 635 may collapse under negative pressure as shown at 638 in FIG. 16B, even though the anvil 636 is only pressing in the center portion perpendicular to the plane of the drawing. A mechanism for preventing this from happening is a cradle formed by a pair of barriers 642 as shown in FIG. 16C. The barriers 642 may pivot (by means of a hinge 644, for example), into position to cradle the valve body 640 when the anvil 636 is forced toward it and out of the way (falling into a recess 646), when a corresponding anvil, such as 636, is forced against the valve body 640.

Referring now to FIGS. 17A through 17D, another actuator mechanism employs a linear actuator 650, which could be, for example, a solenoid, a screw-driven linear actuator, a hydraulic or pneumatic actuator, or other device. The end of the actuator 650 is connected by a pivoting link 667 to a rear pin 669 of a hook anvil 652. The rear pin is guided in a first groove 663. The hook anvil is also guided by another groove 665 into which a forward pin 673 fits. A portion of a valve body 670, which could be any valve body described in the present specification or similar, is held in place over a wall 658 on which a fluid circuit is mounted, of which the valve body 670 is a part. When the linear actuator 650 is activated, the hook anvil 673 rides as guided by the grooves 663 and 665 through the stages shown in the sequence of FIGS. 17A–17D until a tip of the hook anvil presses into the valve body 670 as shown at 671. When the linear actuator 650 is retracted, it rotates out of the way so that a similar mechanism moving in a direction perpendicular to the one shown can pinch the valve body 670 in another direction.

Figure 18A:
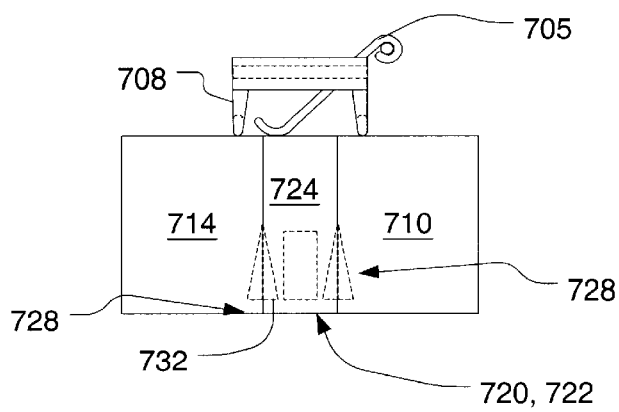
FIGS. 18A–18C illustrate an embodiment of another type of actuator mechanism in a non-actuated (home) configuration.
Figure 18B:
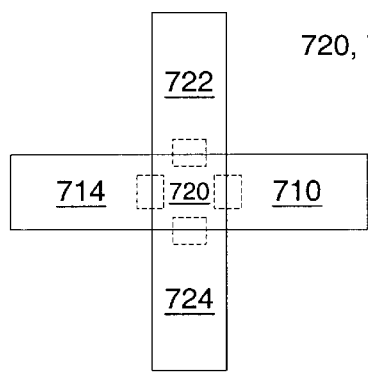
Figure 18C:
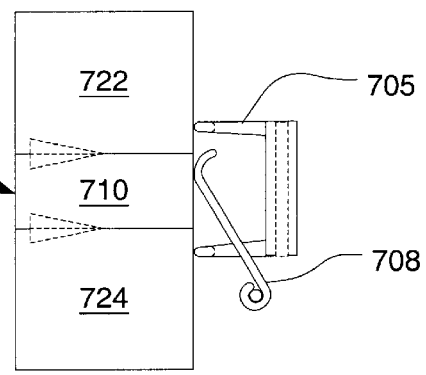
Figure 18D:
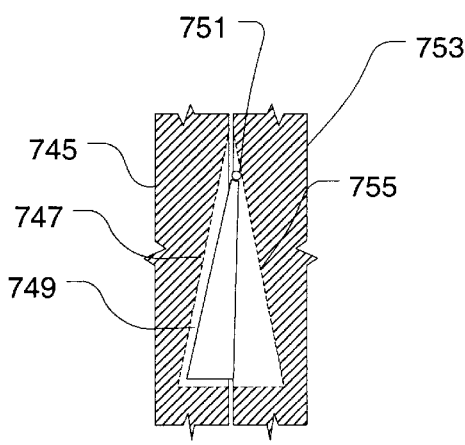
FIGS. 18D and 18E illustrate a ratchet mechanism for use with the embodiment of FIGS. 18A–18C and 18F–18H.
Figure 18E:
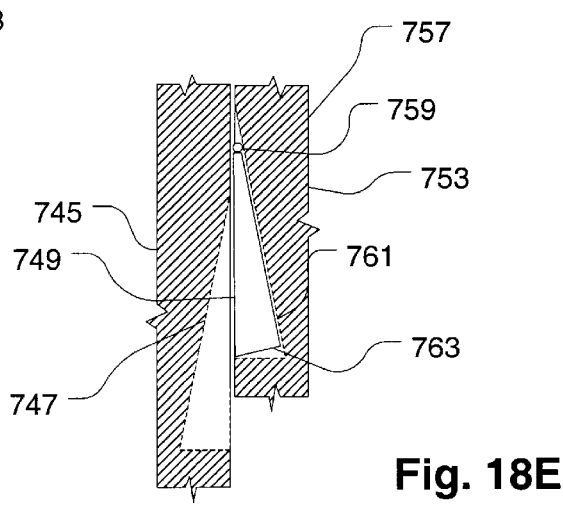

Referring now to FIGS. 18A–18C, another actuator example has anvils 710, 714, 720, 722, and 724 which operate in concert. Each set of flanking anvils 710, 714 and 724, 722 engages the center anvil 720 by means of passive ratchet mechanisms 728. Referring now also to FIGS. 18D and 18E, ratchet mechanisms 728 could be designed as shown with a spring urged catch 749 pivotably mounted by a hinge 751 to one part 753, which could be any of anvils 710, 714, 722, or 724. The catch 749 engages in a recess 747 when the catch 749 and recess 747 are aligned. When part 745 moves forward (the direction is down in the figure), part 753 is free to remain where it is. If part 753 moves forward, the catch 749 engages in the recess 747 and forces part 745 forward with it. In this way, anvil 720 always moves forward whenever a pair of anvils 722, 724 or 710, 714 moves forward, thus forming a contiguous edge to create any of seal regions 415, 416, 450, 451, 620, and 625 in the foregoing figures.

Figure 18F:
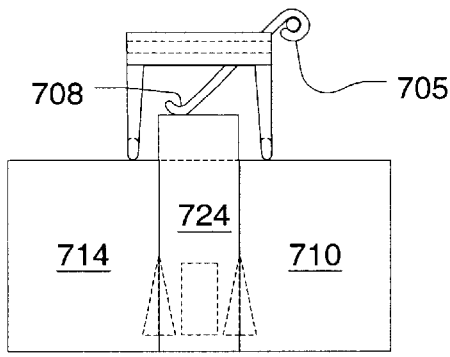
Figure 18J:
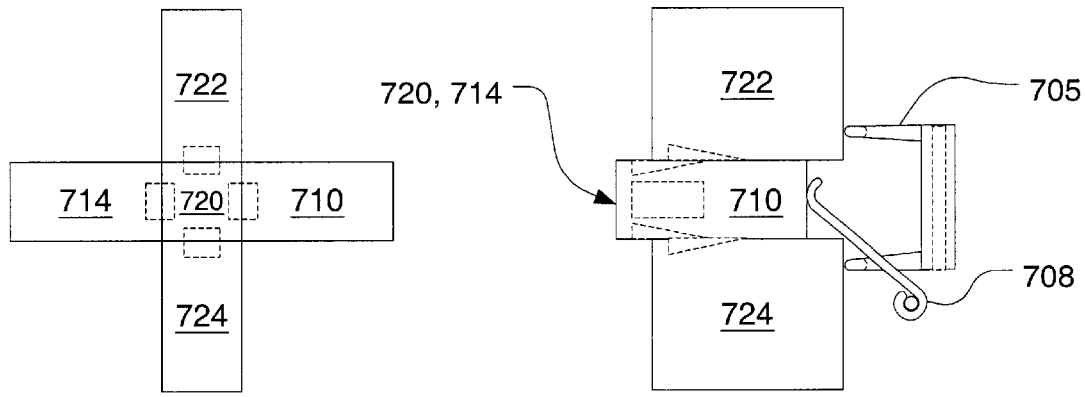
FIG. 18J illustrates components related to the embodiment of FIGS. 18A–18H.
Figure 18J:
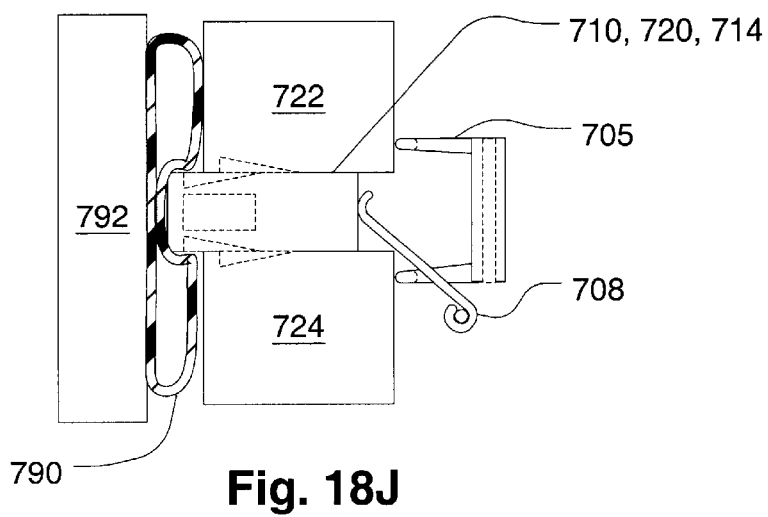

Only one of the sets of flanking anvils 710, 714 and 720, 722 is forced downwardly at a time and each brings the center anvil 720 forward with them. Referring momentarily to FIG. 18J, it is assumed a barrier 792 is provided ahead of the anvils (e.g., 710, 720, 714 as shown in FIG. 18J) to pinch a valve body 790 as they move forward, but this is not shown in all the figures. A pair of rocking cam devices 708 and 705 push the sets flanking anvils 710, 714 and 722, 724, respectively. When rocking cam 708 is rotated, it pushes flanking anvils 710 and 714 forward as illustrated in FIGS. 18F–18G.

It should be clear from the drawings that in the embodiment of FIGS. 18A–18C, 18F–18G, the rocking cams 705 and 708 may be driven by a rotating actuator rather than a linear actuator. Alternatively, linear actuators may be employed to move the anvils 710, 714, 722, and 724.

Figure 19A:
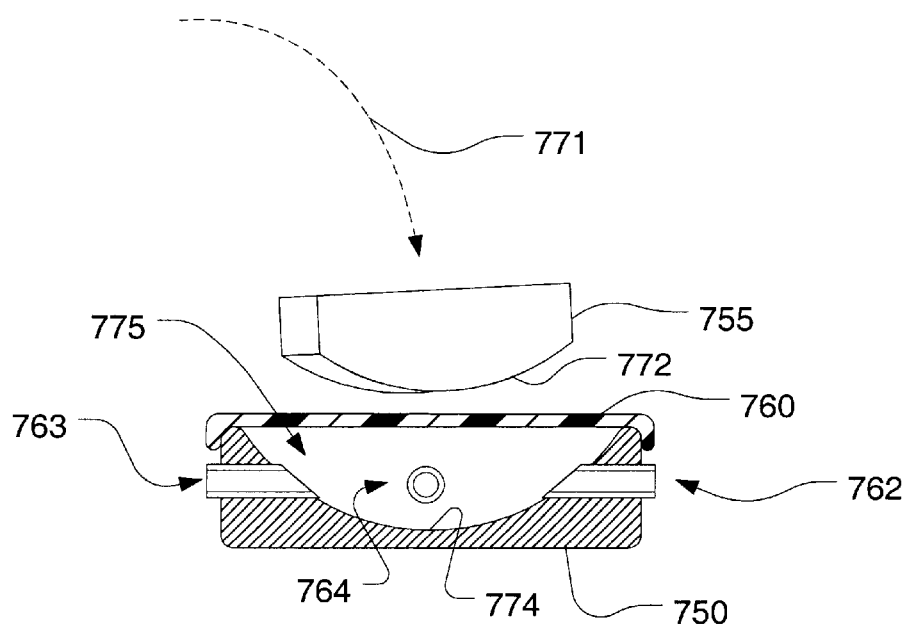
FIGS. 19A–19B show a valve body with a rigid portion and a flexible portion and an alternative type of anvil support/actuator mechanism.
Figure 19B:
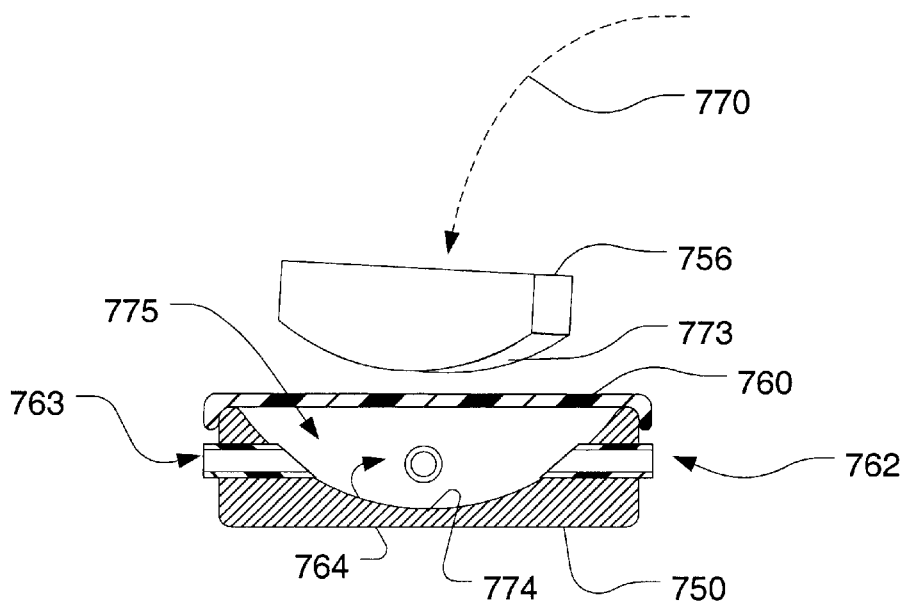

Referring now to FIGS. 19A and 19B, a valve body that has rigid 750 and flexible 760 parts includes ports 762, 763, and 764. A fourth is assumed present to form a four-way valve, but is not visible in the section view. A recess 775 in the rigid portion 750 has a bowl-shaped blind end 774 to which an anvil 755 is conforming in shape. The anvil cuts at a 45 degree angle, pairing the ports so that when anvil 755 with a curved face 772 presses downwardly as indicated by arrow 771, ports 763 and 764 are in flow communication and port 762 and the invisible port are in flow communication. When the anvil 756 with a curved face 773 presses against the flexible portion 760, the corresponding pairing of ports is implemented. The anvils 755 and 756 may be supported on pivotable supports so that they descend like hammers when actuated as shown by the arrows 770 and 771. In this way, each anvil can operate with out interfering with the other.

Referring now also to FIG. 19C, a variation on the design of FIGS. 19A and 19B, helps to insure that the flexible portion 760 of the housing is able to resist negative pressure by providing raised tips 785 that may support the flexible portion under negative pressure. Each port 782–784 (and an invisible one) has a tip as shown at 784. When the anvil 755 presses the flexible portion 785 to seal against the recess 775, the flexible portion 785 is held away from the bowl-shaped blind end 774 surface by the tips 785 providing flow communication between ports not sealed off from each other (e.g., port 783 and 784).

Referring to FIGS. 20A and 20B, the valve bodies of the foregoing embodiments, represented in the present figures generally by the valve body 820, need not be fully self-supporting. It is possible, to provide external supports such as shown at 823, 810, 821, and 828. The supports 823, 810, 821, and 828 engage the valve body 820 and allow the supports 823, 810, 821, and 828 to pull up respective portions when a corresponding anvil 815 or 825 is pushed against the valve body 820. Thus, the valve body 820 is kept from collapsing.

In many of the embodiments discussed above, one or more seals are created inside a flow area of a valve body by pressing one wetted surface of the valve body against another. One of the consequences of defining multiple flow passages using this technique is that the seals for different flow configurations lie along different lines which intersect. Also, at least in some embodiments, the flow runs parallel to the seal. For example seal 65 in FIG. 3A and seal 75 in FIG. 4A have longitudinal aspects that necessarily define intersecting lines and areas that overlap.

Another consequence of forming seals by pressing one wetted surface against another is that it creates narrow dead-end regions where the two wetted surfaces are very close. It is possible that the fluid, for example blood, may coagulate in these regions under certain circumstances. One feature of embodiments described above is that fluid flows past these seal regions so that any small amount of coagulation may be washed away. To prevent excessive coagulation, however, the valve may be operated at a minimum rate to insure that any stagnant blood does not rest for overly long resulting in an excessive buildup of coagulated blood or other fluid factors. This minimum rate may be determined empirically for a given valve configuration, flow rate, treatment duration, etc. It may be that other determinants of a minimum switching time due to the particular application insure that no coagulation will occur. But if that is not the case, it may be necessary to increase the frequency of operation of the valve to insure that some minimum rate of switching occurs such that undue coagulation is prevented.

It will be evident to those skilled in the art that the invention is not limited to the details of the foregoing illustrative embodiments, and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A device for selectively directing flow in a fluid circuit of a blood treatment system, comprising:

a valve body with ports;

said valve body being shaped such that it can be selectively deformed into a first configuration to define at least one first flow channel connecting a first port of said ports to a second port of said ports while isolating said at least one first flow channel from a third port of said ports;

said valve body being shaped such that it can be selectively deformed into a second configuration to define at least one second flow channel connecting said first port to said third port while isolating said at least one second flow channel from said second port;

an actuator having an engagement portion positionable in a first position to selectively deform said valve body in said first configuration and positionable in a second position to selectively deform said valve body in said first configuration;

said first and second flow channels having a substantially constant cross-sectional area from said first port to said second port in said first configuration and from said first to said third in said second configuration; said first and second flow channels including said ports such that a hydraulic diameter is maintained substantially constant from a point in a flow immediately prior to entering said valve body to a point immediately after leaving said valve body such that a flow would experience substantially no mean flow deceleration within said valve body.

2. A device as in claim 1, wherein said first and second flow channels are cylindrical in cross-section.

3. A device as in claim 2, wherein said ports are four in number and said second configuration is such that a third flow channel is defined which connects said second port with a fourth port of said ports.

4. A device as in claim 2, wherein said valve body is selectively deformable by pinching said valve body.

5. A device as in claim 2, wherein said ports are configured to permanently connect with flexible tubing.

6. A device as in claim 2, wherein said valve body has first and second pairs of tubular portions, two of which are simultaneously pinched in each of said first and second configurations.

7. A device as in claim 2, wherein said first and second configurations are defined by a deformation of said valve body along respective lines of pinching.

8. A device as in claim 1, wherein said ports are four in number and said second configuration is such that a third flow channel is defined which connects said second port with a fourth port of said ports.

9. A device as in claim 8, wherein said valve body is selectively deformable by pinching said valve body.

10. A device as in claim 8, wherein said ports are configured to permanently connect with flexible tubing.

11. A device as in claim 8, wherein said valve body has first and second pairs of tubular portions, two of which are simultaneously pinched in each of said first and second configurations.

12. A device as in claim 8, wherein said first and second configurations are defined by a deformation of said valve body along respective lines of pinching.

13. A device as in claim 1, wherein said valve body is selectively deformable by pinching said valve body.

14. A device as in claim 13, wherein said ports are configured to permanently connect with flexible tubing.

15. A device as in claim 13, wherein said valve body has first and second pairs of tubular portions, two of which are simultaneously pinched in each of said first and second configurations.

16. A device as in claim 13, wherein said first and second configurations are defined by a deformation of said valve body along respective lines of pinching.

17. A device for selectively directing flow in a fluid circuit of a blood treatment system, comprising:

a valve body with ports;

said valve body being shaped such that it can be selectively deformed into a first configuration to define at least one first flow channel connecting a first port of said ports to at a second port of said ports while isolating said at least one first flow channel from a third port of said ports;

said valve body being shaped such that it can be selectively deformed into a second configuration to define at least one second flow channel connecting said first port to said third port while isolating said at least one second flow channel from said second port;

an actuator configured to selectively deform said valve body into said first and said second configurations;

said first and second flow channels having a substantially constant cross-sectional area from said first port to said second port in said first configuration and from said first to said third in said second configuration; wherein an interior volume of said valve body is toroidal in shape.

18. A device as in claim 2, wherein said ports are four in number and said second configuration is such that a third flow channel is defined which connects said second port with a fourth port of said ports.

19. A device as in claim 2, wherein said valve body is selectively deformable by pinching said valve body.

20. A device as in claim 2, wherein said ports are configured to permanently connect with flexible tubing.

21. A device as in claim 2, wherein said valve body has first and second pairs of tubular portions, two of which are simultaneously pinched in each of said first and second configurations.

22. A device as in claim 2, wherein said first and second configurations are defined by a deformation of said valve body along respective lines of pinching.

23. A device for selectively directing flow in a fluid circuit of a blood treatment system, comprising:

a valve body with ports;

said valve body being shaped such that it can be selectively deformed into a first configuration to define at least one first flow channel connecting a first port of said ports to a second port of said ports while isolating said at least one first flow channel from a third port of said ports;

said valve body being shaped such that it can be selectively deformed into a second configuration to define at least one second flow channel connecting said first port to said third port while isolating said at least one second flow channel from said second port;

an actuator having an engagement portion positionable in a first position to selectively deform said valve body in said first configuration and positionable in a second position to selectively deform said valve body in said first configuration;

said first and second flow channels having a substantially constant cross-sectional area from said first port to said second port in said first configuration and from said first to said third in said second configuration; wherein said first and second flow channels are cylindrical in cross-section.

24. A device for selectively directing flow in a fluid circuit of a blood treatment system, comprising:

a valve body with ports;

said valve body being shaped such that it can be selectively deformed into a first configuration to define at least one first flow channel connecting a first port of said ports to a second port of said ports while isolating said at least one first flow channel from a third port of said ports;

said valve body being shaped such that it can be selectively deformed into a second configuration to define at least one second flow channel connecting said first port to said third port while isolating said at least one second flow channel from said second port;

an actuator selectively configurable to deform said valve body in said first configuration and to selectively deform said valve body in said first configuration;

said first and second flow channels having a substantially constant cross-sectional area from said first port to said second port in said first configuration and from said first to said third in said second configuration; wherein said valve body has first and second pairs of tubular portions, two of which simultaneously pinched in each of said first and second configurations.

25. A device as in claim 24, wherein said first and second configurations are defined by a deformation of said valve body along respective lines of pinching.

26. A device as in claim 24, wherein said actuator is configured to selectively deform said valve body by urging one movable member into each of said first and second pairs of tubular portions.

27. A device for selectively directing flow in a fluid circuit of a blood treatment system, comprising:

a valve body with ports;

said valve body being shaped such that it can be selectively deformed into a first configuration to define at least one first flow channel connecting a first port of said ports to a second port of said ports while isolating said at least one first flow channel from a third port of said ports;

said valve body being shaped such that it can be selectively deformed into a second configuration to define at least one second flow channel connecting said first port to said third port while isolating said at least one second flow channel from said second port;

an actuator configured to selectively deform said valve body into said first and said second configurations by urging at least one movable member into at least one first portion of said valve body to deform it into said first configuration and by urging said at least one movable member into at least one second portion of said value body to deform it into said second configuration;

said first flow channel and said first and second ports together defining a continuous substantially cylindrical flow path of substantially constant diameter and said second flow channel and said first and third ports together defining a continuous substantially cylindrical flow path of substantially constant diameter.

28. A device as in claim 27, wherein said valve body is toroidal in shape.

29. A device as in claim 28, wherein said ports are four in number and said second configuration is such that a third flow channel is defined which connects said second port with a fourth port of said ports.

30. A device as in claim 28, wherein said valve body is selectively deformable by pinching said valve body.

31. A device as in claim 28, wherein said ports are configured to permanently connect with flexible tubing.

32. A device as in claim 28, wherein said valve body has first and second pairs of tubular portions, two of which are simultaneously pinched in each of said first and second configurations.

33. A device as in claim 28, wherein said first and second configurations are defined by a deformation of said valve body along respective lines of pinching.

34. A device as in claim 27, wherein said ports are four in number and said second configuration is such that a third flow channel is defined which connects said second port with a fourth port of said ports.

35. A device as in claim 34, wherein said valve body is selectively deformable by pinching said valve body.

36. A device as in claim 34, wherein said ports are configured to permanently connect with flexible tubing.

37. A device as in claim 34, wherein said valve body has first and second pairs of tubular portions, two of which are simultaneously pinched in each of said first and second configurations.

38. A device as in claim 34, wherein said first and second configurations are defined by a deformation of said valve body along respective lines of pinching.

39. A device as in claim 27, wherein said valve body is selectively deformable by pinching said valve body.

40. A device as in claim 39, wherein said ports are configured to permanently connect with flexible tubing.

41. A device as in claim 39, wherein said valve body has first and second pairs of tubular portions, two of which are simultaneously pinched in each of said first and second configurations.

42. A device as in claim 39, wherein said first and second configurations are defined by a deformation of said valve body along respective lines of pinching.

43. A device as in claim 27, wherein said valve body has first and second pairs of tubular portions, two of which are simultaneously pinched in each of said first and second configurations.

44. A device as in claim 43, wherein said first and second configurations are defined by a deformation of said valve body along respective lines of pinching.

45. A device as in claim 27, wherein said first and second configurations are defined by a deformation of said valve body along respective lines of pinching.

46. A device for selectively directing flow in a fluid circuit of a blood treatment system, comprising:
- a valve body including four tubular portions linked at ends thereof to define a valve body with toroidal internal volume and with ports linked to said interior volume;
- an actuator in operative association with said valve body, said actuator having at least one movable member that may, in a first configuration of said actuator, be urged simultaneously against two of said tubular portions to selectively deform said valve body into a first configuration to define a first flow channel connecting a first of said ports to a second of said ports and a second flow channel connecting a third of said ports to a fourth of said ports;
- a second configuration of said actuator being effective to deform said valve body into a first configuration to define a third flow channel connecting said first of said ports to said third of said ports and a fourth flow channel connecting said second of said ports to said fourth of said ports.

47. A device as in claim 46, wherein said at least one member includes a single edge that engages said two of said tubular portion in said first configuration of said actuator.

48. A device as in claim 46, wherein said at least one member is pivotably mounted relative to said valve body.

* * * * *